United States Patent
Aspinwall et al.

(10) Patent No.: US 11,073,508 B2
(45) Date of Patent: Jul. 27, 2021

(54) RAPID CONDUCTANCE BASED ION CHANNEL ANALYSIS

(71) Applicant: Arizona Board of Regents on Behalf of the University of Arizona, Tucson, AZ (US)

(72) Inventors: Craig Alan Aspinwall, Tuscon, AZ (US); Steven Scott Saavedra, Tuscon, AZ (US); Mark Tadashi Agasid, Tuscon, AZ (US)

(73) Assignee: Arizona Board of Regents on Behalf of the University Of Arizona, Tuscon, AZ (US)

( * ) Notice: Subject to any disclaimer, the term of this patent is extended or adjusted under 35 U.S.C. 154(b) by 236 days.

(21) Appl. No.: 15/937,253

(22) Filed: Mar. 27, 2018

(65) Prior Publication Data
US 2018/0284098 A1    Oct. 4, 2018

Related U.S. Application Data

(60) Provisional application No. 62/477,578, filed on Mar. 28, 2017.

(51) Int. Cl.
*G01N 33/487* (2006.01)
*G01N 15/10* (2006.01)

(52) U.S. Cl.
CPC ... *G01N 33/48728* (2013.01); *G01N 15/1031* (2013.01)

(58) Field of Classification Search
CPC ......... G01N 33/48728; G01N 15/1031; G01N 25/72; G01N 33/582; G01N 33/06; A61N 1/0408; A61N 1/0452; A61N 1/0484

USPC ....... 324/464, 600, 643–654, 717, 122, 705, 324/671, 693, 525
See application file for complete search history.

(56) References Cited

U.S. PATENT DOCUMENTS

| | | | |
|---|---|---|---|
| 5,234,566 A | 8/1993 | Osman et al. | |
| 6,063,260 A | 5/2000 | Olesen et al. | |
| 6,488,829 B1 | 12/2002 | Schroeder et al. | |
| 2001/0029391 A1* | 10/2001 | Gluckman ......... | A61N 1/36014 607/2 |
| 2002/0063067 A1 | 5/2002 | Bech et al. | |
| 2011/0160074 A1* | 6/2011 | Wood ..................... | C40B 40/04 506/9 |

(Continued)

OTHER PUBLICATIONS

Enhanced Temporal Resolution with Ion Channel-Functionalized Sensors using Conductance-Based Measurement Protocol, Anal. Chem. 2017,89,1315-1322 (Year: 2017).*

(Continued)

*Primary Examiner* — Melissa J Koval
*Assistant Examiner* — Trung Q Nguyen
(74) *Attorney, Agent, or Firm* — Hylton-Rodic Law PLLC

(57) ABSTRACT

Ligand-ion channel interactions are analyzed via electrophysiological methods having rapid temporal response and high sensitivity, thereby reducing the collection time and enabling monitoring of dynamic processes. This protocol allows quantification of ligand concentrations in the sub-millisecond to ms range, as compared to s-min for traditional approaches. Moreover, the method can be easily integrated into existing patch clamp analysis packages and allow for monitoring of rapid, dynamic chemical processes in a feasible manner.

20 Claims, 40 Drawing Sheets

(56) References Cited

U.S. PATENT DOCUMENTS

2012/0208174 A1* 8/2012 Galush ............ G01N 33/54346
435/5

OTHER PUBLICATIONS

Aspinwall, Craig, et al., Enhanced Temporal Resolution with Ion Channel-Functionalized Sensors Using a Conductance -Based Measurement Protocol, Anal. Chem. 2017, 89, 1315-1322 (2016).
Denyer J., et al., HTS approaches to voltage-gated ion channel drug discovery, Drug Discovery Today, vol. 3, Issue 7, Jul. 1, 1998, pp. 323-332 (abstract).
Hanns-J. Neubert, Patch Clamping Moves to Chips, Analytical Chemistry, 327A-330A (2004).
Jana Kusch and Giovanni Zifarell, Patch-Clamp Fluorometry: Electrophysiology meets Fluorescence, Biophysical Journal, vol. 106,1250-1257 (2014).
Yu, Hai-bo, et al., High throughput screening technologies for ion channels, Acta Pharmacologica Sinica (2016) 37: 34-43.
Zhao, Y., et al., Patch clamp technique: review of the current state of the art and potential contributions from nanoengineering, Proc. IMechE vol. 222, 1-11, Part N: J. Nanoengineering and Nanosystems.

* cited by examiner

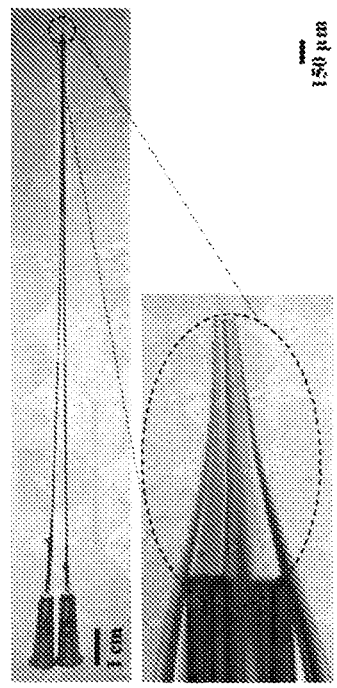
FIG. 1A-B

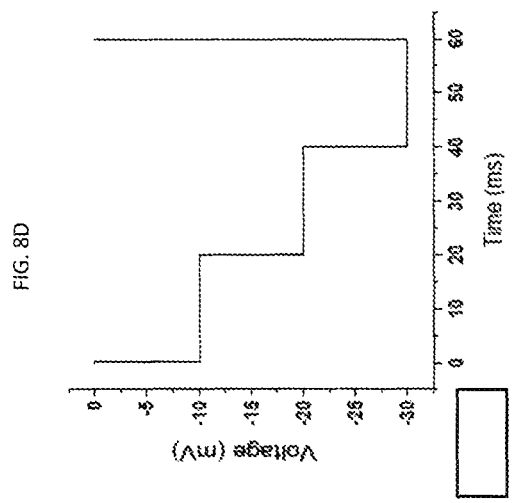

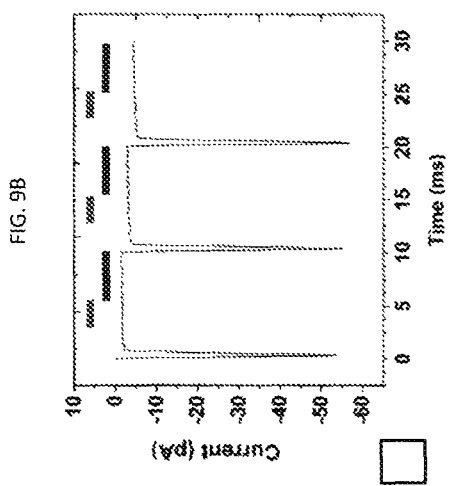

RAPID CONDUCTANCE BASED ION CHANNEL ANALYSIS

CROSS-REFERENCE TO RELATED APPLICATION

This application claims the benefit of U.S. Provisional Application No. 62/477,578, filed Mar. 28, 2017, which is incorporated herein by reference in its entirety.

GOVERNMENT SUPPORT

This invention was made with government support under Grant No. R01 EB007047 awarded by NIH. The government has certain rights in the invention.

FIELD OF THE INVENTION

The present invention relates to a method for obtaining electrophysiological measurements of ligand-ion channel interactions with millisecond temporal resolution. The approach utilizes rapid time-resolved monitoring of ion channel modulated membrane conductance.

BACKGROUND OF THE INVENTION

Cell-based assays can be used in many applications, such as identification of new targets, screening for safety and efficacy, and monitoring changes in cell-based activities. Innovations in high-throughput screening and robotic systems have made the process of drug discovery less time-consuming and efficient. Ion channels (IC) are a major focus for drug discovery, as well as for preclinical safety screening. Ion channels are membrane-spanning molecules that regulate the flow of ions by opening a channel, thus allowing tiny and quick currents that must be measured directly to assess the impact on the cell. Indirect measurements are possible with fluorescent dyes or spectroscopy, but direct measurements require a technique referred to as patch clamping. Label-free detection of analytes lacking optical (e.g. fluorescence) or electrochemical activity presents a number of challenges for rapid, sensitive analysis in complex samples.

Electrophysiological assays provide one of the most direct and accurate ways to characterize ion channel activity by measuring a current or a voltage difference between two electrodes. IC-functionalized sensor platforms require a lipid bilayer, usually a black lipid membrane (BLM) or planar lipid bilayer, to ensure proper IC function. In the patch clamp technique, one of the electrodes is in contact with a solution on one side of the lipid membrane, whereas the other electrode is placed in a solution on the other side of the lipid membrane. This electrode configuration allows the operator to control the voltage across the membrane and measure currents that flow across the membrane. Drugs can be applied to the solution and their effect on the currents, and thus the ICs, can be measured. Binding of a target analyte to an IC modulates the ion flux through the IC, which can then be detected electrochemically, providing label-free detection with single-molecule selectivity and often with very high specificity due to the nature of ligand-IC interactions.

Comparatively little effort has been devoted to preparing IC-functionalized sensors with rapid temporal response and high sensitivity. This is important in measuring dynamic biological processes that occur on the millisecond (ms) to second (s) timescale. Previous advancements in ion channel analysis technology are focused largely on enhancing the throughput and improving capabilities for multiple measurements. For both stochastic nanopore sensors and ligand-gated ICs, sensitivity improves as the number of reconstituted ICs increases, though greater numbers of ICs obscure single channel dynamics often utilized for ligand quantitation.

In the most common IC-functionalized sensor analysis protocols, either stochastic or ligand-gated IC activity is monitored as changes in quantized current flux across the BLM due to individual blockade events or opening/closings of a small number (e.g. 1-5) of ICs. Due to the ability to resolve ion flux through a single IC, this method is referred to as single channel recording. During measurements, the membrane is held at a constant potential for >30 s (and up to several minutes) to obtain an ensemble of open/closed or blockade events of the IC. Acquiring recordings as a function of ligand/analyte concentration can generate dose-response curves to assess IC activity. Measurements requiring minutes to perform cannot monitor many dynamic biological processes, such as single cell exocytosis, which occur on the millisecond to second timescale. The collection time required to obtain statistically valid measurements during single channel recordings restricts the accessible temporal regime while the requisite small numbers of ICs limits sensitivity and dynamic range.

Conversely, monitoring the activity of many channels simultaneously allows measurement of the net membrane conductance. As ligands bind to and dissociate from ICs, the net ion flux across the membrane is modulated in a concentration-dependent manner. The membrane conductance is measured from the slope of an i-V curve, generated from the steady state membrane current as a function of applied voltage (V). The acquisition rate of this approach is limited by two factors. First, the capacitive charging of the membrane that occurs upon a step change in voltage must decay sufficiently prior to measuring IC current. Second, membrane currents must be sampled at several voltages to obtain the slope of the i-V curve. While the conductance measurement protocol is more complex than the single channel recording protocol, it may be more reproducible because: a) a larger number of ICs can be monitored which enhances S/N, b) the integration of multiple ICs reduces the effects of IC rundown and inactivation, and c) the membrane conductance is calculated from measurements at multiple applied voltages, thus averaging noise at a given potential. Furthermore, since dose-response curves are based on normalized membrane conductance in the presence and absence of ligand, lipid bilayers containing differing numbers of reconstituted ICs may be compared. In contrast, single channel recordings depend on absolute channel activity.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

The binding of a target analyte to an IC, which is readily detected electrochemically in a label-free manner with single-molecule selectivity and specificity, has generated widespread interest in using natural and engineered ICs as transducers in biosensing platforms. To date, the majority of developments in IC-functionalized sensing have focused on IC selectivity or sensitivity, or development of suitable membrane environments and aperture geometries. Comparatively little work has addressed analytical performance criteria, particularly criteria required for collecting quantitative IC-functionalized sensor responses and measurements of dynamic processes with millisecond temporal resolution.

This invention recognizes a different aspect for improvement and demonstrates an approach for acquiring chemical measurements in ion channel functionalized sensors or other ion channel functionalized membranes, e.g. cell membranes, wherein ion channel-ligand binding is measured with a rapid temporal response and high sensitivity. Through identification and subsequent optimization of key experimental parameters, conductance-based measurements of gated-IC activity were performed with sub-millisecond to millisecond temporal resolution, a timescale enabling the measurement of fast, dynamic biological processes.

In one aspect, the present invention encompasses a method of obtaining ion channel measurements from an IC functionalized sensor platform. The method may comprise a) providing the IC-functionalized sensor platform comprising a pipette and a lipid membrane suspended on a pipette aperture of the pipette, b) placing the IC-functionalized sensor platform in a solution such that the lipid membrane is disposed in the solution, c) continuously applying a voltage set to the IC-functionalized sensor platform via the amplifier, and d) measuring a conductance of the lipid membrane. A plurality of ion channels may be embedded in the lipid membrane. The IC-functionalized sensor platform is operatively connected to an amplifier. The voltage set may comprise a plurality of consecutive voltages that are applied in a step-wise pattern so as to alternate between decreasing and increasing voltages. Each voltage may be rapidly applied for a short duration pulse. In some embodiments, a net time required to measure the conductance is about 10-50 ms. In some embodiments, a net time required to measure the conductance is about 0.5-1.5 ms.

In another aspect, the present invention encompasses a method of obtaining ion channel measurements from an ion channel (IC) functionalized sensor platform. The method may comprise a) providing the IC-functionalized sensor platform comprising an apparatus with an aperture and a lipid membrane suspended on the aperture, b) placing the IC-functionalized sensor platform in a solution such that the lipid membrane is disposed in the solution, continuously applying a voltage set to the IC-functionalized sensor platform via the amplifier, and measuring a conductance of the lipid membrane. A plurality of ion channels may be embedded in the lipid membrane. The IC-functionalized sensor platform may be operatively connected to an amplifier. The voltage set can comprise a plurality of consecutive voltages that are applied in a step-wise pattern so as to alternate between decreasing and increasing voltages. Each voltage may be rapidly applied for a short duration pulse. In some embodiments, a net time required to measure the conductance is about 10-50 ms. In some embodiments, a net time required to measure the conductance is about 0.5-1.5 ms.

In some embodiments, the method may further comprise a step of adding an analyte to the solution, wherein measuring the conductance comprises measuring a first conductance after the analyte is added to the solution. In any of the above embodiments, measuring the conductance may further comprise measuring a second conductance before the analyte is added to the solution. In any of the above embodiments, measuring the conductance of the lipid membrane may comprise measuring the conductance of a black lipid membrane. In any of the above embodiments, measuring the conductance of the lipid membrane may comprise measuring the conductance of a cell membrane or a fragment thereof.

It is an objective of the present invention to analyze ligand-ion channel interactions via electrophysiological methods used to prepare ion-channel functionalized sensors with rapid temporal response and high sensitivity, thereby reducing the collection time and enabling monitoring of dynamic processes. This approach is unique in that it allows quantification of ligand concentrations in less than 30 milliseconds as compared to seconds to minutes for traditional approaches. Moreover, it can be easily integrated into existing patch clamp analysis packages and allow for monitoring of rapid, dynamic chemical processes and/or more rapid screening of drugs that modulate ion channels in a feasible manner.

Key features of this protocol include the reduction of membrane area and the use of small voltage steps (10 mV) and short duration voltage pulses (10 ms), which have the net effect of reducing the capacitive charging and decreasing the time required to achieve steady state currents. Rapid conductance measurements are broadly applicable to IC-based sensors that undergo analyte-specific gating. In one embodiment, application of a conductance protocol employing three sequential, 10 ms voltage steps in an alternating, pyramid-like arrangement enabled sampling of membrane conductance every 30 milliseconds. As will be described herein, use of this protocol in dynamic IC measurements on black lipid membranes (BLMs) functionalized with an IC, Gramicidin A (gA) were conducted using a fast perfusion system. BLM conductance decreased by 76±7.5% within 30 ms of switching from solutions containing 0 to 1 M $Ca^{2+}$, which demonstrates the feasibility of using this approach to monitor rapid, dynamic chemical processes.

BRIEF DESCRIPTION OF THE DRAWINGS

The features and advantages of the present invention will become apparent from a consideration of the following detailed description presented in connection with the accompanying drawings in which:

FIGS. 1A-1D show Illustration of the fast solution exchange setup. FIG. 1A is an image of the theta capillary perfusion tip. FIG. 1B is a 40× magnified image of the theta capillary outlet. FIG. 1C shows the BLM/pipette and theta capillary positioned close to each other using two micropositioners, M1 and M2. Solutions for the experiment are supplied by a syringe pump (not shown) flowing at 50 µL/min through 100 µm i.d. glass capillaries that feed the two channels of the theta glass. FIG. 1D is a schematic of the BLM/pipette tip and theta capillary tip region. Solution exchange is achieved by holding the BLM/pipette tip at a stationary position, while M2 is rastered to direct different solutions across the BLM/pipette tip.

FIG. 8A-8F shows multistep voltage protocols A-F, respectively. Multistep voltage protocols B-E were assessed with respect to reference protocol A. Voltage protocol F represents a modification of protocol E which can be continuously looped.

FIG. 9B shows current trace measured using protocol E for the same BLM. The solid lines above the trace indicate intervals of 3-5 ms (blue) and 5-10 ms (red) after each voltage step.

FIG. 14A shows single channel recordings of gA at a holding potential of −100 mV, showing characteristic single channel currents. Data was filtered at 200 kHz for presentation purposes. FIG. 14B is a proposed sub-ms voltage protocol, employing 3 voltage steps, holding each step for 1 ms. FIG. 14C shows a resulting current plot from FIG. 14B. FIG. 14D shows mean membrane currents calculated from various time points along the 1 ms voltage pulse versus applied voltage.

FIG. 15A is an optimized sub-millisecond voltage protocol. FIG. 15B shows a tradition voltage protocol implementing voltage steps from −100 mV to +100 mV in 10 mV steps. Note: A 1 s segment intended for the BLM to discharge is not shown in between each voltage step, for clarity.

DETAILED DESCRIPTION

Figure 1C:
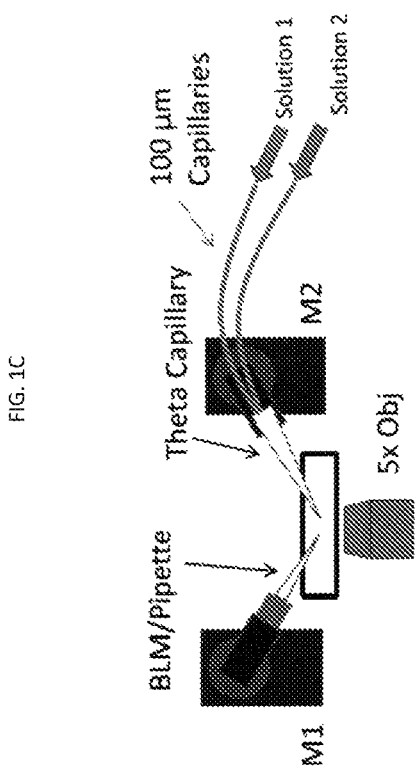
Figure 1D:
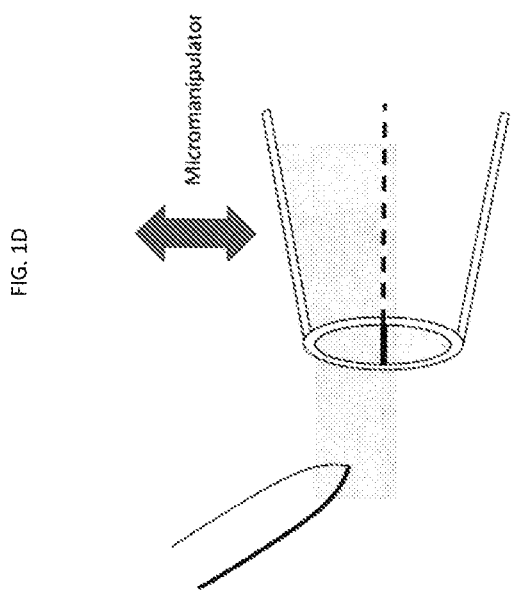

As used herein, the term "a step in voltage" is defined as a voltage difference between one voltage level and a subsequent voltage level. A "decreasing" voltage step (as illustrated, for example in FIG. 8F) refers to a voltage step from a higher (or less-negative) voltage to a lower (or more-negative) voltage. An "increasing" voltage step (as illustrated, for example in FIG. 8F) refers to a voltage step from a lower (or more-negative) voltage to a higher (or less-negative) voltage.

As used herein, the term "step-wise pattern" refers to a predefined sequence of voltage pulses having a predefined duration and magnitude. "Step-wise pattern" includes steps to higher (or less-negative) voltages, steps to lower (or more-negative) voltages, and combinations thereof. In some embodiments, as used herein "step-wise pattern" may refer to instances where the voltage set comprises a plurality of consecutive voltages that are applied in a step-wise pattern (e.g., a "stairstep" pattern), so as to alternate between decreasing and increasing voltages, thereby forming a multistep or pyramid-like sequence.

As used herein, the term "placing the IC-functionalized sensor platform in a solution such that the lipid membrane is disposed in the solution" refers methods involving contacting a lipid membrane with a solution that contains and/or is intended to receive an analyte that may effect a change of conductivity of the lipid membrane. The contact between the lipid membrane and the solution does not necessarily require that any portion of the IC-functionalized sensor platform other than the lipid membrane is placed in contact with or immersed in (either entirely or partially) the solution.

The term "suspended on" as used herein in the phrases "suspended on a pipette aperture" and "suspended on the aperture" refers generally to the position of the lipid membrane relative to that of the aperture of an apparatus (such as a pipette) and includes embodiments of the invention where a lipid member is suspended on an aperture of apparatus (such as a pipette) as well as embodiments of the invention where a lipid member is suspended across an aperture of apparatus (such as a pipette).

Referring now to FIGS. 1-16, the present invention features a method of obtaining ion channel measurements from an ion channel (IC) functionalized sensor platform. In one embodiment, the method may comprise providing the IC-functionalized sensor platform comprising a pipette and a lipid membrane suspended on a pipette aperture of the pipette. Preferably, a plurality of ion channels may be embedded in the lipid membrane. In another preferred embodiment, the IC-functionalized sensor platform is operatively connected to a power source, such as an amplifier. The method further comprises placing the IC-functionalized sensor platform in a solution such that the lipid membrane is disposed in the solution, continuously applying a voltage set to the IC-functionalized sensor platform via the amplifier, and measuring a conductance of the lipid membrane.

Figure 8A:
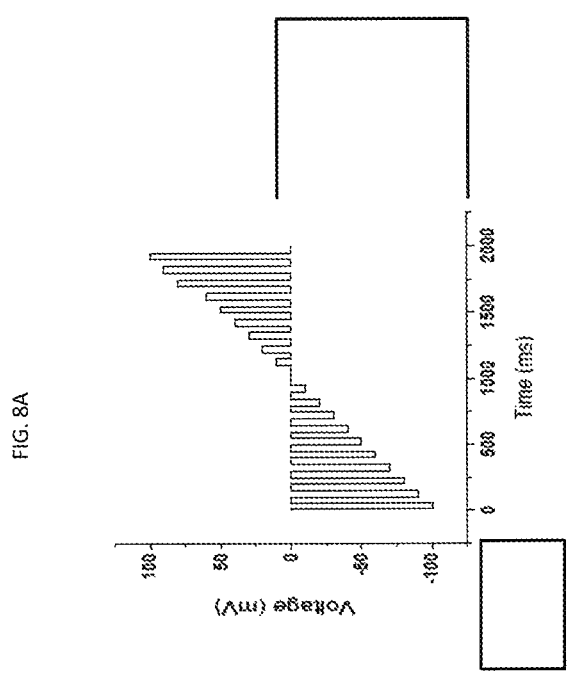
Figure 8B:
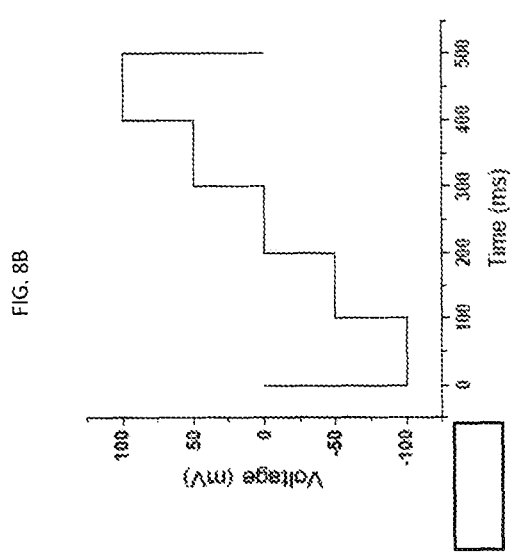
Figure 8C:
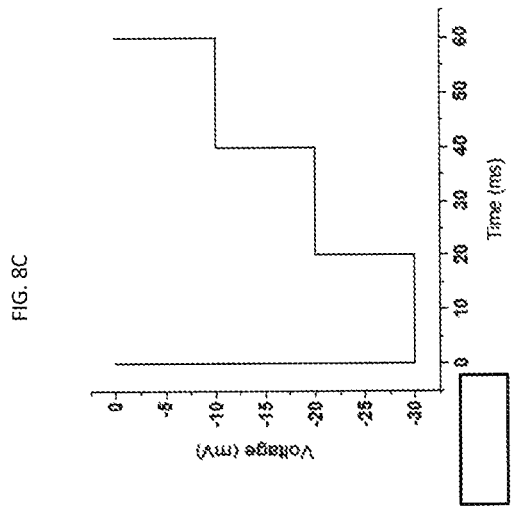
Figure 8E:
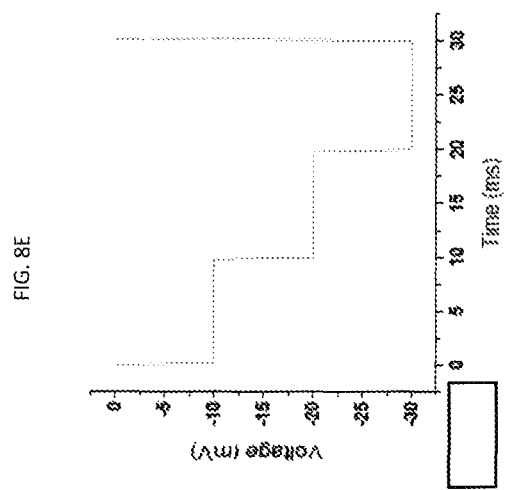
Figure 8F:
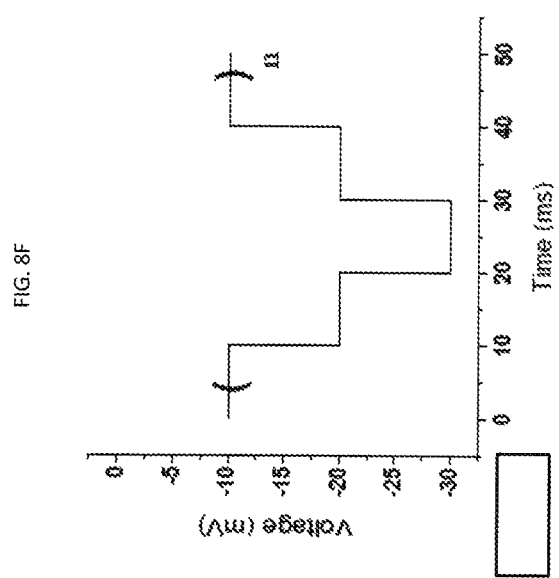

In a preferred embodiment, the voltage set may comprise a plurality of consecutive voltages that are applied in a step-wise pattern (e.g., a "stairstep" pattern), so as to alternate between decreasing and increasing voltages, thereby forming a pyramid-like sequence. FIGS. 8B-8F show non-limiting examples of consecutive voltage pulses that form stepwise (stairstep) patterns of increasing voltages (e.g., FIGS. 8B and 8C), decreasing voltages (FIGS. 8D and 8E), and both decreasing and increasing voltages (FIG. 8F). Each voltage is rapidly applied for a short duration pulse. In some embodiments, the voltage set may comprise about 2-5 voltage steps for each decreasing or increasing run of voltages (i.e., about 2-5 increasing voltage steps and about 2-5 decreasing voltage steps). For example, for a decreasing voltage levels, the number of voltage steps may be about 3 voltage steps. Then, the voltage levels may be set to increase by about 3 voltage steps. In other embodiments, each voltage step can range from about 5-15 mV. For instance, a voltage step may be set to increase or decrease in increments of about 10 mV. In further embodiments, the short duration pulse may range from about μs to ms in time. In one embodiment, for example, the short duration pulse may range from about 5-15 ms. In another embodiment, the short duration pulse may range from about 200-400 μs. It is understood that the present invention is not limited to the aforementioned examples, and that any step size, number of steps, or pulse values may be used as long the resulting pattern forms a multi-step sequence. It is contemplated that other short-duration pulse sequences with alternate shapes, including curved and or linear increases and decrease may also be utilized in place of a stair-step pattern.

One of the unique, technical features of the present invention is the use of rapid and continuous application of the stair-case voltage pattern to generate a conductance value, rather than the traditional single point in time current measurement or integrated fixed potential current measurements. Without wishing to limit the invention to a particular theory or mechanism, the method is effective for reducing capacitive charging and decreasing a time required to achieve steady state currents and to measure the conductance, as compared to a single time point conductance measurement or integrated fixed potential conductance measurements. In preferred embodiments, the method may be effective for decreasing the time required to achieve steady state currents and measure the conductance to a millisecond time range, instead of seconds or minutes.

The net time required to achieve steady state currents and measure the conductance according to the method of the present invention may be from about 0.5 ms to about 100 ms. In some embodiments, the net time to measure the conductance ranges from about 0.5 ms to about 50 ms. In some embodiments, the net time to measure the conductance ranges from about 0.5 ms to about 1.5 ms. In some embodiments, the net time to measure the conductance ranges from about 0.5 ms to about 5 ms. In some embodiments, the net time to measure the conductance ranges from about 0.5 ms to about 10 ms. In some embodiments, the net time to measure the conductance ranges from about 0.5 ms to about 15 ms. In some embodiments, the net time to measure the conductance ranges from about 0.5 ms to about 20 ms. In some embodiments, the net time to measure the conductance ranges from about 0.5 ms to about 25 ms. In some embodiments, the net time to measure the conductance ranges from about 0.5 ms to about 30 ms. In some embodiments, the net time to measure the conductance ranges from about 0.5 ms to about 40 ms. In some embodiments, the net time to measure the conductance ranges from about 5 ms to about 10 ms. In some embodiments, the net time to measure the conductance ranges from about 5 ms to about 20 ms. In some embodiments, the net time to measure the conductance ranges from about 5 ms to about 30 ms. In some embodiments, the net time to measure the conductance ranges from about 5 ms to about 40 ms. In some embodiments, the net time to measure the conductance ranges from about 5 ms to about 50 ms. In some embodiments, the net time to measure the conductance ranges from about 10 ms to about 15 ms. In some embodiments, the net time to measure the conductance ranges from about 10 ms to about 20 ms. In some embodiments, the net time to measure the conductance ranges from about 10 ms to about 30 ms. In some embodiments, the net time to measure the conductance ranges from about 10 ms to about 40 ms. In some embodiments, the net time to measure the conductance ranges from about 10 ms to about 50 ms.

In some embodiments, the net time to measure the conductance ranges from about 50 ms to about 100 ms. In some embodiments, the net time to measure the conductance ranges from about 50 ms to about 80 ms. In some embodiments, the net time to measure the conductance ranges from about 50 ms to about 70 ms. In some embodiments, the net time to measure the conductance ranges from about 50 ms to about 60 ms. In some embodiments, the net time to measure the conductance ranges from about 60 ms to about 100 ms. In some embodiments, the net time to measure the conductance ranges from about 70 ms to about 90 ms.

In some embodiments, when an analyte is added to the solution while the voltage set is continuously applied, the method allows for a concentration of the analyte to be determined from the measured conductance. For example, the method may be configured for use in any ion channel measurement application, including, but not limited to, patch clamp analysis or in drug-ion channel binding.

Analysis of ion-channel modulating ligands (analytes) involves the integration of a lipid bilayer that is positioned between two fluid compartments. The lipid bilayer forms an electrically resistive seal and also serves as the platform for reconstitution of the ion channels. Thus, current measured across the membrane is generated by ion flux through the ion channel. Subsequent activation or inhibition of the ion channel upon analyte binding can lead to a change in ion flux through an individual channel that is manifest as a concentration-dependent net change in conductance across the lipid bilayer.

In some embodiments, a method of the present invention may further comprise a step of adding an analyte to the solution into which the lipid membrane of the IC-sensor platform is placed. In these embodiments, measuring the conductance of the lipid membrane comprises measuring a first conductance after the analyte is added to the solution. Optionally, in any of these embodiments, measuring the conductance of the lipid membrane further can comprise measuring a second conductance before the analyte is added to the solution.

Measuring the first conductance of the lipid membrane provides a conductance value that may be used to determine (e.g., by calculation) a quantity of analyte in the solution (e.g., the quantity of analyte that was added to the solution). A person having ordinary skill in the art will recognize this determination when implemented in combination with a calibration step may be used to calculate a concentration of the analyte that is effective to modulate ion channel activity.

In other embodiments, the IC-functionalized sensor platform is part of an automated system. For example, the pipette may be held in the solution by a pipette holder. Preferably, the pipette holder has a reduced length that is effective to reduce noise contributions from the pipette holder.

In one embodiment, a diameter of the pipette aperture is about 1-5 μm. For example, the diameter of the pipette aperture may be about 3 μm. In some embodiments, a coating may be applied to the pipette such that the surface of the pipette is compatible with the lipid membrane and/or such that charging is reduced. For example, in another embodiment, the pipette aperture may be silanized to support the lipid membrane. In yet another embodiment, the pipette aperture may be coated with a siloxane compound to minimize capacitive charging effects.

In further embodiments, a coating may be applied to the apparatus with an aperture such that the surface of the apparatus is compatible with the lipid membrane and/or such that charging is reduced. In some embodiments, the aperture of the apparatus may be silanized to support the lipid membrane. In yet another embodiment, the aperture of the apparatus may be coated with a siloxane compound to minimize capacitive charging effects.

According to some embodiments, the plurality of ion channels may be transmembrane proteins. The number of ion channels may range from about 3 to 15 ion channels. However, it is understood that the number of ion channels is not limited to these values, and that it can be selected to a desired amount in order to reduce a signal-to-noise ratio. In one embodiment, for example, the conductance measurement may be collected at about 200 kHz and filtered at about 1 kHz. The lipid membrane may comprise at least about 5 consistently active ion channels in order to obtain a signal-to-noise ratio of at least about 3. In another embodiment, the conductance measurement may be collected at about 200 kHz and filtered at about 10 kHz. The lipid membrane may comprise at least about 10 consistently active ion channels in order to obtain a signal-to-noise ratio of at least about 3.

In some aspects, the invention includes an IC-functionalized sensor platform wherein a pipette is used to provide the aperture across which a lipid membrane is suspended to measure conductance across the membrane. For example, the suspended lipid membrane forms a high-resistance seal in the aperture. In addition to the aperture, the pipette provides a reservoir in which a solution (e.g., a recording buffer as described herein) may be placed in simultaneous fluid contact with the lipid membrane and an electrode used to measure the conductance across the membrane. It is contemplated that other apparatuses may be used in place of a pipette in an IC-functionalized sensor platform used in various embodiments of the present invention. Thus, suitable other apparatuses comprise an aperture across which the lipid membrane is suspended and, optionally, comprise a reservoir in which a solution can be placed to provide simultaneous fluid contact between the lipid membrane and an electrode. Other suitable apparatuses include, but are not limited to a needle, a needle array, a pipette array, a microcapillary tube, a microcapillary array, a microwell, a microwell array, a planar substrate (e.g., a polymer (e.g., polytetrafluoroethylene (PTFE)), an oxide, glass, a metal oxide, etc.) having an aperture, and a planar substrate having a plurality of isolated apertures with the proviso that each aperture of the plurality of isolated apertures can have an electrical measurement performed on it at a fixed point in time.

In some embodiments of the present invention, the lipid membrane in the IC-functionalized sensor platform may be a synthetic (e.g., artificial) membrane. A nonlimiting example of a synthetic membrane used in the IC-functionalized sensor platform of the present invention is a black lipid membrane (BLM).

In some embodiments of the present invention, the lipid membrane in the IC-functionalized sensor platform may be a biological membrane such as a cell membrane, for example, or a fragment thereof.

Ion channels serve as targets for a wide range of physiological and pharmacological agents and are primary targets for the treatment of diseases. The methods of the present invention may be used to detect or quantify one or more molecules that interacts with a protein in a lipid membrane, or the lipid components of the membrane, to produce to change in transmembrane current and conductance. In some embodiments, the present invention can be used to screen for physiological and pharmacological modulators of ion channel activity, including, but not limited to, drugs used to treat diabetes, epilepsy, migraine headaches, neuropathic pain, ataxia and others. Among these drugs include broad classes such as sulfonylureas, sodium channel blockers, beta-blockers, $Ca^{2+}$ channel blockers and others.

EXEMPLARY EMBODIMENTS

Embodiment A is a method of obtaining ion channel measurements from an ion channel (IC) functionalized sensor platform, said method comprising:
a. providing the IC-functionalized sensor platform comprising a pipette and a lipid membrane suspended on a pipette aperture of the pipette, wherein a plurality of ion channels is embedded in the lipid membrane, wherein the IC-functionalized sensor platform is operatively connected to an amplifier;
b. placing the IC-functionalized sensor platform in a solution such that the lipid membrane is disposed in the solution;
c. continuously applying a voltage set to the IC-functionalized sensor platform via the amplifier, wherein the voltage set comprises a plurality of consecutive voltages that are applied in a step-wise pattern so as to alternate between decreasing and increasing voltages, wherein each voltage is rapidly applied for a short duration pulse; and
d. measuring a conductance of the lipid membrane;
wherein a net time required to measure the conductance is about 0.5 ms to about 50 ms.

Embodiment B is the method of Embodiment A, wherein a diameter of the pipette aperture is about 1-5 μm.

Embodiment C is the method of Embodiment A or Embodiment B, wherein the voltage set comprises about 2-5 increasing voltage steps and about 2-5 decreasing voltage steps.

Embodiment D is the method of Embodiment A or Embodiment B, wherein the voltage set comprises about 2-5 voltage steps for each decreasing or increasing run of voltages.

Embodiment E is the method of any one of the preceding Embodiments, wherein the method is effective for decreasing the time required to achieve steady state currents and measure the conductance to a millisecond time range.

Embodiment F is the method of any one of the preceding Embodiments, wherein each voltage step ranges from about 5-15 mV.

Embodiment G is the method of any one of the preceding Embodiments, wherein the short duration pulse ranges from about 5-15 ms.

Embodiment H is the method of Embodiment G, wherein a net time required to measure the conductance is about 10-50 ms.

Embodiment I is the method of Embodiment H, wherein the lipid membrane comprises at least about 5 consistently active ion channels.

Embodiment J is the method of any one of Embodiments A through F, wherein the short duration pulse ranges from about 200-400 µs.

Embodiment K is the method of Embodiment J, wherein a net time required to measure the conductance is about 0.5-1.5 ms.

Embodiment L is the method of Embodiment K, wherein the lipid membrane comprises at least about 10 consistently active ion channels.

Embodiment M is the method of any one of the preceding Embodiments, wherein the conductance measurement is collected at about 200 kHz and filtered at about 10 kHz.

Embodiment N is the method of any one of the preceding Embodiments, wherein a signal-to-noise ratio is at least about 3.

Embodiment O is the method of any one of the preceding Embodiments, wherein the pipette is held in the solution by a pipette holder, wherein the pipette holder has a length effective to reduce noise.

Embodiment P is the method of any one of the preceding Embodiments, wherein the pipette aperture is silanized.

Embodiment Q is the method of any one of the preceding Embodiments, wherein the pipette aperture is coated with a siloxane compound.

Embodiment R is a method of obtaining ion channel measurements from an ion channel (IC) functionalized sensor platform, said method comprising:
  a. providing the IC-functionalized sensor platform comprising an apparatus with an aperture and a lipid membrane suspended on the aperture, wherein a plurality of ion channels is embedded in the lipid membrane, wherein the IC-functionalized sensor platform is operatively connected to an amplifier;
  b. placing the IC-functionalized sensor platform in a solution such that the lipid membrane is disposed in the solution;
  c. continuously applying a voltage set to the IC-functionalized sensor platform via the amplifier, wherein the voltage set comprises a plurality of consecutive voltages that are applied in a step-wise pattern so as to alternate between decreasing and increasing voltages, wherein each voltage is rapidly applied for a short duration pulse; and
  d. measuring a conductance of the lipid membrane wherein a net time required to measure the conductance is about 0.5 ms to about 50 ms.

Embodiment S is the method of Embodiment R, wherein a diameter of the aperture is about 1-5 µm.

Embodiment T is the method of Embodiment R or Embodiment S, wherein the voltage set comprises about 2-5 increasing voltage steps and about 2-5 decreasing voltage steps.

Embodiment U is the method of Embodiment R or Embodiment S, wherein the voltage set comprises about 2-5 voltage steps for each decreasing or increasing run of voltages.

Embodiment V is the method of any one of Embodiments R through U, wherein the method is effective for decreasing the time required to achieve steady state currents and measure the conductance to a millisecond time range.

Embodiment W is the method of any one of Embodiments R through V, wherein each voltage step ranges from about 5-15 mV.

Embodiment X is the method of any one of Embodiments R through W, wherein the short duration pulse ranges from about 5-15 ms.

Embodiment Y is the method of Embodiment X, wherein a net time required to measure the conductance is ranges from about 10-50 ms.

Embodiment Z is the method of Embodiment Y, wherein the lipid membrane comprises at least about 5 consistently active ion channels.

Embodiment AA is the method of any one of Embodiments R through Y, wherein the short duration pulse ranges from about 200-400 µs.

Embodiment AB is the method of Embodiment AA, wherein a net time required to measure the conductance is about 0.5-1.5 ms.

Embodiment AC is the method of Embodiment AB, wherein the lipid membrane comprises at least about 10 consistently active ion channels.

Embodiment AD is the method of any one of Embodiments R through AC, wherein the conductance measurement is collected at about 200 kHz and filtered at about 10 kHz.

Embodiment AE is the method of any one of Embodiments R through AD, wherein a signal-to-noise ratio is at least about 3.

Embodiment AF is the method of any one of Embodiments R through AE, wherein the aperture is silanized.

Embodiment AG is the method of any one of Embodiments R through AF, wherein the aperture is coated with a siloxane compound.

Embodiment AH is the method of any one of Embodiments R through AG, wherein the apparatus further comprises a reservoir in fluid communication with the aperture.

Embodiment AI is the method of any one of the preceding Embodiments, further comprising a step of adding an analyte to the solution, wherein the measuring the conductance comprises measuring a first conductance after the analyte is added to the solution.

Embodiment AJ is the method of Embodiment AI, wherein the measuring the conductance further comprises measuring a second conductance before the analyte is added to the solution.

Embodiment AK is the method of any one of the preceding Embodiments, wherein the measuring the conductance of the lipid membrane comprises measuring the conductance of a black lipid membrane.

Embodiment AL is the method of any one of the preceding Embodiments, wherein the measuring the conductance of the lipid membrane comprises measuring the conductance of a cell membrane or a fragment thereof.

Example 1

The following is a non-limiting example of conductance-based measurements of gated-IC activity performed with enhanced temporal resolution. Equivalents or substitutes are within the scope of the invention.

Experimental

Chemicals and Materials:

KCl, $CaCl_2$, 2-[4-(2-hydroxyethyl)piperazin-1-yl]ethane sulfonic acid (HEPES), and Gramicidin A (gA) were purchased from Sigma Aldrich (St. Louis, Mo.). 3-(Cyanopropyl)-dimethylchlorosilane was purchased from TCI America (Portland, Oreg.). 1,2-Diphytanoyl-sn-glycero-3-phosphocholine (DPhPC) was purchased from Avanti Polar Lipids (Alabaster, Ala.). $HNO_3$ was purchased from Mallinckrodt (St Louis, Mo.). Ethanol (EtOH) was purchased from Decon Labs (King of Prussia, Pa.) and acetonitrile (ACN) was purchased from EMD Millipore (Darmstadt, Germany). All compounds were used as received.

Pipette fabrication and modification of large aperture pipettes: 1.5 mm (o.d.)×1.0 mm (i.d.) borosilicate capillaries (World Precision Instruments, Saratosa, Fla.) were pulled to a sharp tip using a Sutter Flaming-Brown P-97 micropipette puller (Sutter Instruments, Novato, Calif.), broken to an opening of ca. 150 µm in diameter, and fire polished using a Narashige MF-900 microforge (Narashige, Japan) to produce a nominal aperture diameter of 20 µm. Prior to use, individual pipette diameters were measured via microscopy. All large aperture pipette experiments described herein were performed with a single pipette to minimize technical variation.

Pipette Fabrication and Modification of Small Aperture Pipettes:

Small aperture pipettes were prepared using a multi-step heating/pulling process that generated an aperture of ca. 10 µm. Pressure polishing was then performed to produce a tapered geometry with a 3-6 µm aperture. In this process, 40-60 psi is applied to the pipette by compressing air in a 10 mL plastic syringe while the tip is simultaneously fire-polished. The desired angle and aperture size can be achieved by controlling the air pressure and duration. After fabrication, the exterior of small aperture pipettes was coated with Sylgard 184 (Dow Corning Corporation, MI) beginning ca. 200 µm above the tip for 2-3 mm to minimize the effects of capacitive charging of the thin glass near the tip.

Silanization of Pipettes:

Both large and small aperture pipettes were silanized to support BLM formation. Briefly, pipettes were soaked in 0.1 M $HNO_3$ for 30 minutes, followed by rinsing consecutively with $H_2O$, ethanol (EtOH) and dry acetonitrile (ACN). Pipettes were backfilled with 2% (v/v) 3-(cyanopropyl)-dimethylchlorosilane in ACN and stored in the same solution for 12 h. Pipettes were then rinsed consecutively with ACN, EtOH, and $H_2O$, followed by drying in air. Pipettes were best silanized at ambient relative humidity (RH)≤30%. In higher humidity conditions, pipettes were heated at 120° C. for 1 h and then immediately transferred to a Terra Universal humidity control box (Anaheim, Calif.) set at RH=15% for silanization.

Lipid Preparation and BLM Formation:

DPhPC Dissolved in Chloroform was Dried under a gentle stream of Ar and lyophilized overnight. Dried lipid was resuspended in n-decane to a final concentration of 10 mg/mL. BLMs were formed at room temperature (22° C.) and RH≤30%.

BLM Formation on Large Aperture Pipettes:

Lipids were deposited on the interior walls of the pipette by filling the pipette with ~1 µL of lipid solution via the aperture and applying a gentle stream of air to disperse the solution into the pipette. Pipettes were then backfilled with recording buffer (1.0 M KCl, 5 mM HEPES, pH 7.4). The pipette aperture was submerged into a bath solution (recording buffer) and 1 µL lipid solution was applied near the aperture at the pipette tip. A disposable, plastic pipette tip was gently dragged across the aperture, then the aperture/pipette was briefly withdrawn and then submersed in the bath to remove excess lipid. If a BLM was not formed after submersion, a fresh disposable pipette tip was dragged across the aperture to thin the lipid film. BLM formation was verified by applying a 1 V, 10 ms pulse which caused the BLM to rupture and return to open aperture resistance (ca. 20 kΩ). When the aperture was clogged, e.g. by a lipid/decane plug, the voltage pulse was insufficient to yield the characteristic, large decrease in resistance. When a BLM was present, it reformed spontaneously after rupture or after dragging a fresh pipette tip across the aperture.

BLM Formation on Small Aperture Pipettes:

BLMs were formed on small aperture pipettes using a tip-dip process. The pipette was first backfilled with recording buffer and then submerged in the bath solution. At the surface of the bath, 1 µL of lipid solution was applied near the pipette tip, and then the pipette was raised slowly out of the solution to remove excess lipid and then quickly re-immersed. A large increase in resistance was observed, typically from less than 100 kΩ to greater than 50 GΩ, and BLM formation was verified by applying a 1V, 10 ms pulse which caused BLM rupture. Quickly withdrawing and re-immersing the pipette in the bath solution was sufficient to reform the BLM.

Single Channel Recordings, BLM Conductance Measurements, and Analysis of BLM Capacitive Currents:

All electrophysiological measurements were performed using a HEKA Electronik EPC-10 Double patch clamp amplifier (Germany) using PatchMaster software (v2.73). Data were digitized at 20 kHz and filtered at 1 kHz, unless otherwise specified. BLM conductance was measured using several multi-step voltage protocols. All protocols were evaluated against a 21-point reference protocol that applied 50 ms potential pulses ranging from −100 to +100 mV, in 10 mV intervals. Each pulse was preceded by a 10 ms rest at a holding potential of 0 mV and followed by a 1000 ms rest to ensure the bilayer capacitance was fully discharged before proceeding to the next potential step. The slope of the i-V curve is the BLM conductance, $G_{BLM}$ (pA/mV), and the resistance, $R_{BLM}$, is $(G_{BLM})^{-1}$.

A 1 mg/mL stock solution of gA in EtOH was prepared and stored at 4° C. for up to two weeks. For use, the solution was diluted to 1 µg/mL in EtOH and 0.5-1 µL aliquots were injected into the bath solution at a position ca. 5 mm from the pipette tip while monitoring current at a holding potential of −100 mV. The process was repeated until the desired number of gA channels was incorporated into the BLM. Upon incorporation of the desired number of channels in the BLM, the solution was rapidly diluted then exchanged to prevent further monomer incorporation into the BLM.

Estimation of Input Capacitance:

Capacitive currents from the amplifier, electrode, pipette, and pipette holder (input capacitance) were estimated using an established technique, whereby a pipette filled with recording buffer (1 M KCl, 5 mM HEPES, pH 7.4) was depressed several micrometers against a ball of Sylgard 184 adhered at the bottom of a 35 mm petri dish. Seal resistances were typically >200 GΩ. Voltage pulses 200 ms long and ranging from −100 mV to +100 mV in 10 mV steps were applied, and current traces were digitized at 50 kHz and filtered at 1 kHz. These traces, assigned the input capacitance, were subtracted from traces measured with pipettes (submerged to the same depth in recording buffer) that were functionalized with BLMs, yielding traces assigned to the BLM. A single pipette was used to minimize variability in pipette geometry and bilayer area.

Determining BLM Capacitance:

To determine BLM capacitance contributions, BLMs were held at a DC offset and a 10 Hz square wave was applied. Capacitive currents were integrated and charge was converted to capacitance by normalizing the charge to the known capacitance in the model cell, MC-10 (HEKA Elektronik). BLM capacitance as a function of applied voltage was found to follow the equation:

$$C_m = C_0(1+\alpha V_m^2) \qquad \text{Equation 1}$$

where $C_m$ is the membrane capacitance at a particular voltage, $C_0$ is the membrane capacitance at 0 mV, $\alpha$ is fitting variable, and $V_m$ is the membrane voltage.

Response Time Measurements and Analysis:

A dual-port perfusion apparatus was fabricated from a two-barrel theta capillary. A dual-port perfusion apparatus (FIG. 1A) was fabricated from a 1.5 mm o.d.×1.1 mm i.d. borosilicate, two-barrel theta capillary (Sutter Instruments, Novato, Calif.) pulled to a thin tip using a pipette puller. The capillary tip was broken to produce two outlets, each 50-100 µm i.d., using an approach similar to that described for 20 µm apertures. Fused silica capillary tubing, 365 µm o.d.×100 µm i.d. (Polymicro, Phoenix, Ariz.), was inserted into the backside of each barrel of the theta glass pipette and sealed with cyanoacrylate glue. The other end of each capillary tube was glued into the opening of a blunt 20-gauge, luer-fitted needle to provide a connection to a syringe. A dual syringe pump (Harvard Instruments) provided solutions to the perfusion tip at a rate of 50 µL/min. The capillary tip was mounted on a micromanipulator (Sutter Instruments, Model MP225) which was used to laterally translate the tip at a rate of 3 mm/sec over a distance of ca. 70 µm to rapidly switch between solutions in ≤30 ms. The two flow channels of the theta capillary were used to deliver recording buffer or $Ca^{2+}$ solution (1 M $CaCl_2$ dissolved in recording buffer, pH 7.4) to the tip of a pipette backfilled with recording buffer. The 10-90% response time of the solution exchange was determined by laterally translating the theta capillary tip to alternately deliver recording buffer and $Ca^{2+}$ solution to the pipette tip, which was positioned ~200 µm from the outlet of the theta capillary tip, while monitoring the change in current through the pipette aperture at a holding potential of −20 mV.

Results and Discussion

To perform dynamic measurements, IC-functionalized sensors must display acquisition rates at least twice as frequent as the dynamic process under investigation. The temporal dynamics of IC-functionalized sensors are complex, with at least three factors accounting for the net response: a) mass transport dynamics at low analyte concentration, b) binding kinetics and subsequent conformational changes between IC-ligand pairs, and c) the rate at which statistically valid measurements can be obtained. The present invention focuses on the latter in an effort to reduce the overall data acquisition time per measurement and enable more rapid conductance-based analysis. To minimize the effects of mass transfer and binding kinetics, a model channel, gA, was utilized, which yields a conductance similar to native, ligand-gated ICs, and is rapidly and reversibly blocked by high concentrations of $Ca^{2+}$ in a manner that mimics ligand gating.

Conductance-based measurements of IC activity monitor channel currents at a series of discrete voltage steps. Transitioning between voltage steps results in capacitive charging currents which must be dissipated prior to the IC current measurement. Increasing the discharge durations increases the total acquisition time by a factor proportional to the number of steps required for accurate, reproducible conductance measurements. To increase the temporal resolution of conductance-based measurements, three major criteria were investigated here: a) the duration of each step as a function of applied voltage, b) the magnitude of each voltage step, and c) the number of voltage steps.

Figure 2A:
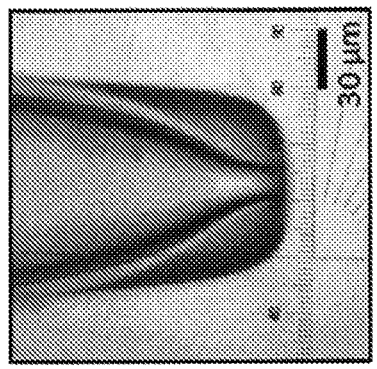
FIG. 2A shows a micrograph of a glass pipette with a 23 µm aperture.
Figure 2B:
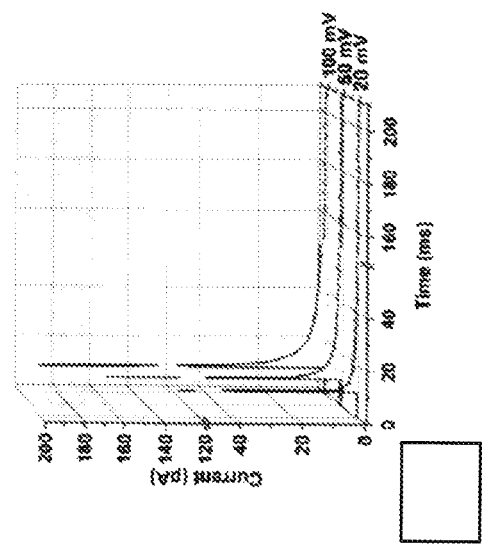
FIG. 2B shows capacitive charging traces for a pipette functionalized with a BLM, composed of Diphytanoylphosphatidylcholine (DPhPC), as a function of applied potential. Steady state currents were background subtracted from each trace for clarity.

Comparison of Aperture Size and Capacitive Charging Characteristics:

The capacitive charging as a function of applied voltage was evaluated for BLMs prepared using DPhPC suspended across glass pipette apertures having an approximate diameter of 20 µm (FIG. 2A). Representative current traces recorded upon application of voltage steps of 20, 50 and 100 mV are shown in FIG. 2B. In these measurements, the BLM was maintained at 0 mV for 10 ms, at which point the indicated voltage was applied for a total duration of 200 ms. Capacitive current traces from the BLM obtained after subtracting the background charging currents due to the glass and amplifier components are plotted in FIG. 2C, and described further below. The peak capacitive charging current and relaxation time (defined as the time for capacitive currents to decrease below 3× noise) as a function of applied voltage are plotted in FIG. 2D. The peak current and relaxation time correlated with the applied voltage, with the relaxation time exhibiting greater variability with increasing voltage. These data show that the magnitude and duration of the capacitive charging presents a major limitation to performing rapid conductance-based measurements of IC activity, which relies upon measurement of steady-state current.

The capacitive charging characteristics of the amplifier and BLM/pipette platform were examined to better understand their contributions at different time regimes. A summary is provided here, with a more detailed discussion in Supporting Information. The BLM/pipette platform is analogous to the membrane patch/patch pipette system used in the patch clamp technique. Both systems may be described by the equivalent circuit shown in FIG. 3, which is comprised of four circuit elements: $C_p$, the total capacitance at the amplifier input (pipette, electrode, etc.); $R_a$, the series resistance resulting from the aperture geometry near the pipette tip; and $R_m$ and $C_m$, the BLM resistance and capacitance, respectively.

Figure 4A:
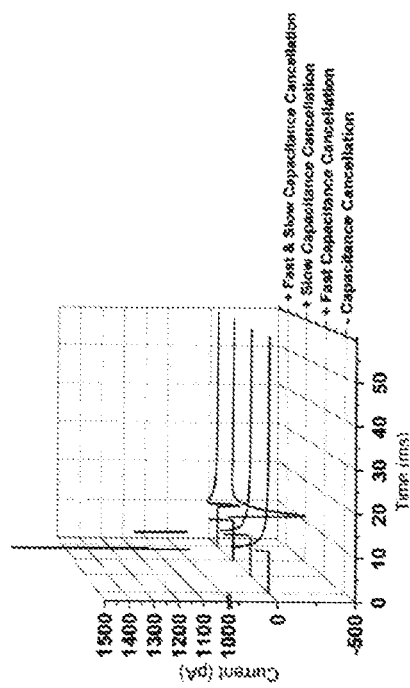
FIGS. 4A-4B show current traces obtained from a DPhPC BLM suspended across a 20 μm aperture with capacitance cancellation (FIG. 4A) and series resistance compensation (FIG. 4B).
Figure 4B:
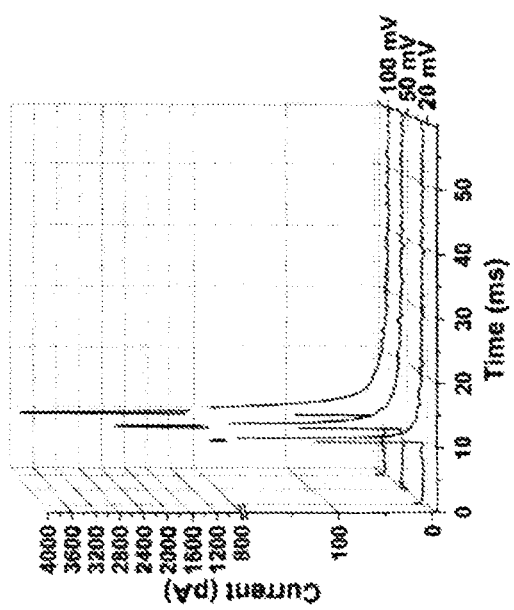

To reduce the capacitive charging that accompanies application of a potential to a membrane suspended across an aperture, patch clamp amplifiers have integrated capacitance cancellation circuitry. Typically, a capacitor, electrically connected to the pipette, injects current in opposition to the charging current using user-defined time constants to account for fast charging components (input capacitance) and slow components (patch membrane). This circuit allows estimation and correction of capacitive charging composed of two RC time constants. In general, the use of two-component capacitance cancellation was insufficient. Specifically, introducing sufficient "slow" capacitance to reduce capacitive charging at time periods longer than 10 ms led to overcompensation of current at times <10 ms (FIGS. 4A-4B). The overcompensation appeared as a negative current that increased to a steady-state current.

The use of the series resistance compensation circuit, a common feature in patch clamp amplifiers, allows application of a brief overpotential at the start of a voltage step to accelerate capacitive charging. While a reduction in capacitive charging time was obtained with series resistance circuitry, the large current spikes at the beginning of the potential steps were typically >300 pA in magnitude and required >5 ms to decay to <2 pA, even at lower applied potentials. When using series resistance compensation (FIG. 4B), no significant acceleration in capacitive charging for timescales <10 ms was observed.

Figure 5A:
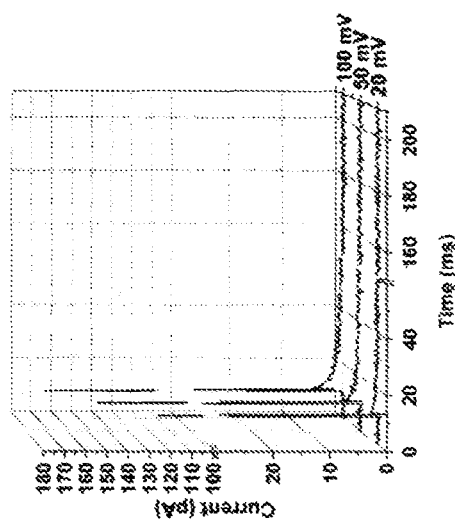
FIGS. 5A-5B show capacitive currents of pipettes lacking a BLM and sealed with Sylgard 184 measured at three applied voltages for 20 μm aperture pipette (FIG. 5A) and 3 μm aperture pipette (FIG. 5B).
Figure 5B:
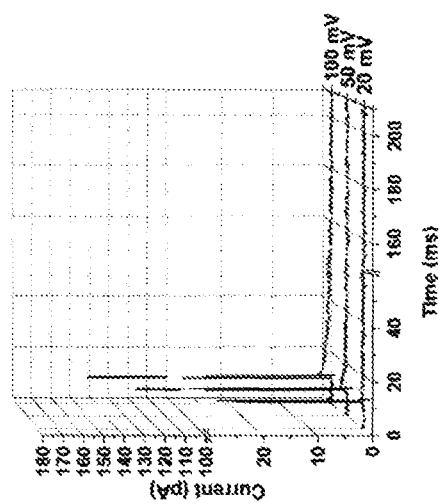

As previously described, the input capacitive current was isolated using an established technique, and then subtracted from the capacitive current for pipettes functionalized with BLMs to yield the portion assigned to the BLM. The contribution of the BLM to the total capacitive decay was estimated by measuring and subtracting $C_p$ (FIGS. 5A-5B). $C_p$ is the major contributor to the initial current spike observed upon application of the voltage step, contributing ~200 pA of current at the initiation of a potential step, which relaxed within ca. 1 ms with a 1 kHz filter setting. Slower charging components are also observed in the traces.

Figure 2C:
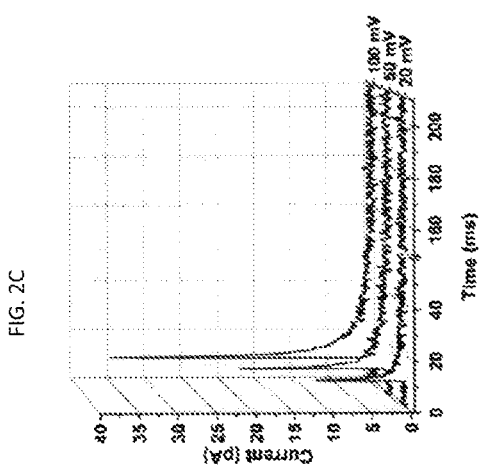
FIG. 2C shows capacitive charging traces for a DPhPC BLM as a function of applied potential after subtraction of capacitive charging contributions from the pipette and the amplifier.
Figure 2D:
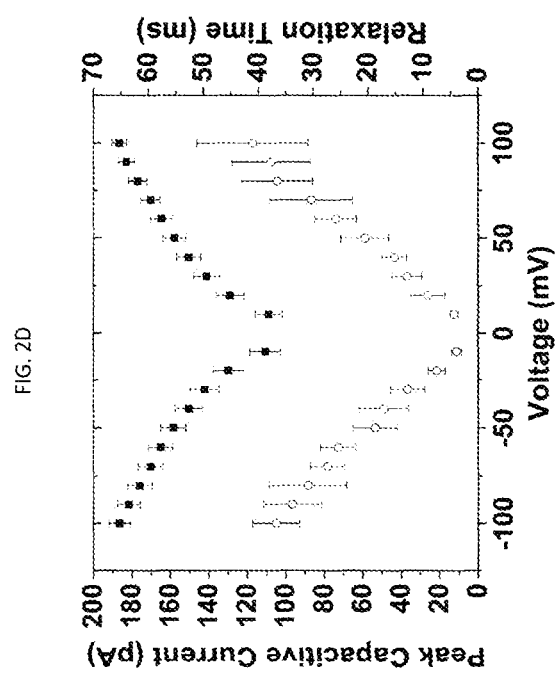
FIG. 2D shows peak capacitive charging currents (black squares) and relaxation times (red circles) for the BLM/pipette platform as a function of applied voltage (n=4).
Figure 3:
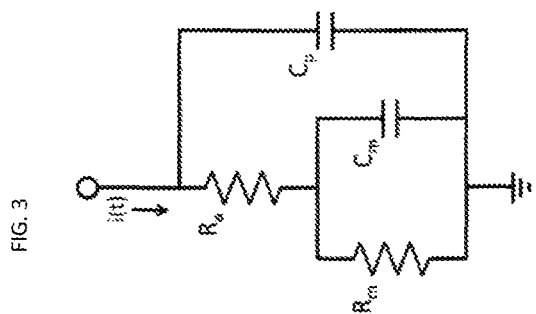
FIG. 3 shows an equivalent circuit for the BLM/pipette platform. $C_p$ represents the input capacitance of the pipette, electrode, etc. $R_a$ represents the resistance associated with the aperture geometry. $R_m$ and $C_m$ represent the resistance and capacitance of the BLM, respectively.
Figure 6:
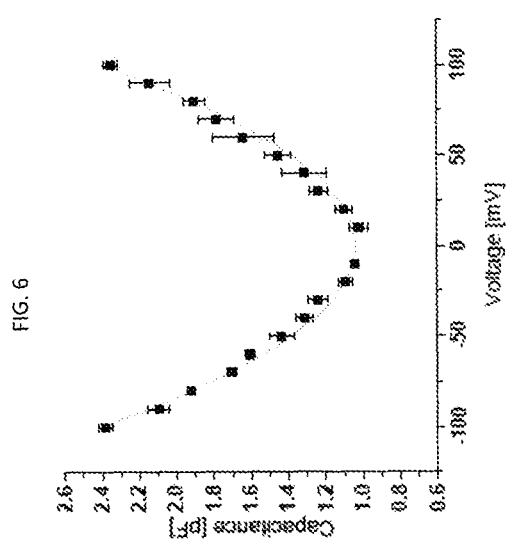
FIG. 6 shows membrane capacitance as a function of applied potential.

The BLM contribution, plotted in FIG. 2C, dominates capacitive charging in the 2-40 ms regime. Integration of the BLM capacitance showed a parabolic dependence on applied voltage (FIG. 6). The voltage-dependence of BLM capacitance follows a quadratic function described by Equation 1 ($r^2$=0.991). From 0 mV to 100 mV, BLM capacitance increased by a factor of 2.5, with $C_0$=0.915+0.003 pF and $\alpha$=1.36+0.03×$10^2$ $V^{-2}$, with no effect on voltage polarity. The non-linear behavior results from equilibration of the solvent in the BLM and the solvent annulus. This non-linear voltage dependence suggests the BLM does not behave as an ideal capacitor. Quantitatively, $C_p$ contributes a capacitance similar to that of the BLM (ca. 2.5 pF at 100 mV); however, the slower charging of the BLM is the rate limiting step. Capacitance cancellation and series resistance compensation were implemented in an effort to reduce the BLM charging contribution. This approach was effective for cancelling a majority of the current spikes at short timescales 2 ms), but did not significantly decrease the charging decay time, particularly in the time regime>20 ms.

Figure 7A:
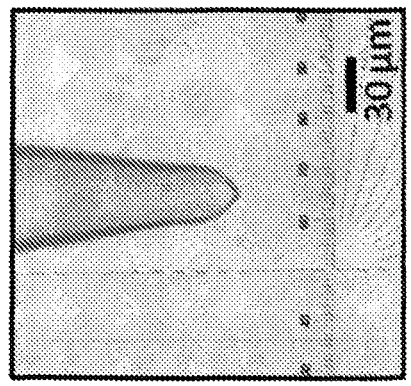
FIG. 7A shows a micrograph of a representative glass pipette with a ca. 3 μm aperture.

An established method to reduce capacitive charging in BLMs is to reduce BLM surface area. Thus pipettes were prepared with aperture diameters of 3-6 µm, (FIG. 7A). This geometry necessitated two modifications due to the thin glass walls near the pipette aperture. First, to minimize pipette/aperture breakage, a gentler method for BLM formation was employed to replace the painting method. Referred to as the tip-dip method, the pipette aperture is passed twice through a lipid monolayer deposited at an air-aqueous buffer interface. Using this approach, DPhPC readily formed high resistance BLMs (>100 GΩ) on silanized, small aperture pipettes. Second, a coating of Sylgard 184 was applied near the pipette tip to compensate for the additional capacitance arising from the thinner glass walls near the tip, compared to the larger diameter, forged apertures.

Figure 7B:
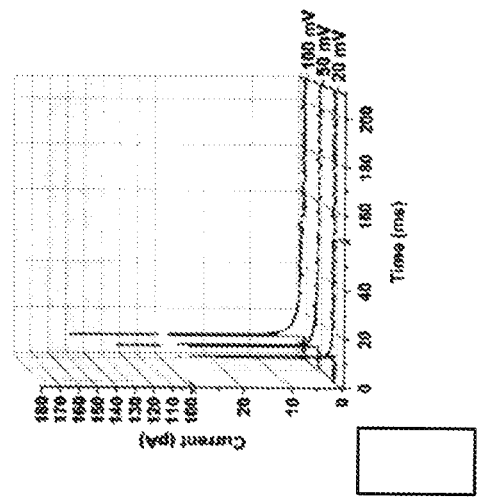
FIG. 7B shows capacitive charging traces for a pipette functionalized with a DPhPC BLM as a function of applied potential. Steady state currents were background subtracted from each trace for clarity.
Figure 7C:
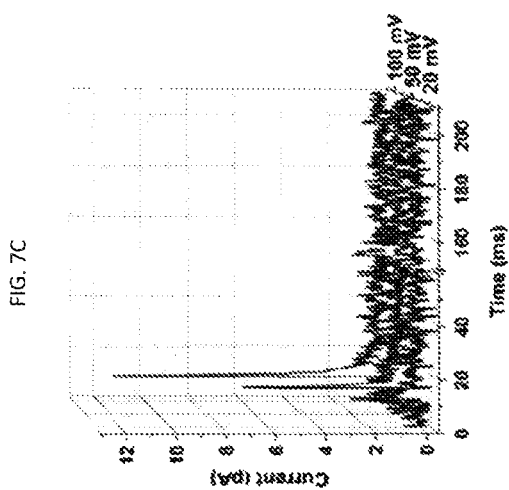
FIG. 7C shows capacitive charging traces for a DPhPC BLM as a function of applied potential following subtraction of capacitive charging contributions from the pipette and the amplifier.
Figure 7D:
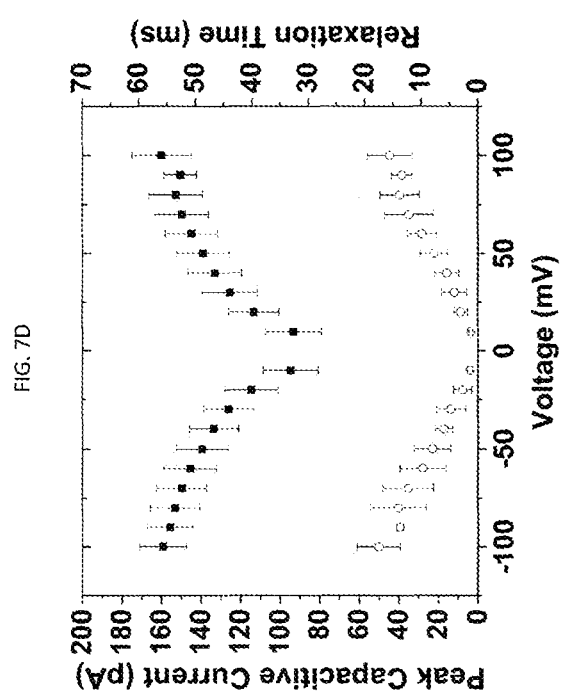
FIG. 7D shows peak capacitive charging currents (black squares) and relaxation times (red circles) for the BLM-functionalized pipette as a function of applied voltage (n=5).

FIG. 7B shows typical capacitive current traces for representative voltages applied to a BLM suspended across a 3 µm aperture pipette; FIG. 7C shows the background-subtracted traces assigned to the BLM. In this smaller geometry, BLM capacitive currents contributed less than pipette currents (FIG. 5B). The peak capacitive currents and relaxation times for BLMs using this aperture geometry are plotted as a function of applied voltage in FIG. 7D. While the peak currents are similar in magnitude to those measured for pipettes with 20 µm apertures, charging relaxation times are approximately 3-fold faster for the smaller apertures. Notably, voltage steps from 0 mV to 10 mV relax within ~1 ms, which should facilitate faster measurements of steady state currents.

Overall, reducing the bilayer area produced three significant outcomes. First, a significant decrease in capacitive charging was observed, particularly for small potential steps. At times greater than 4 ms after application of the potential step, the magnitude of the charging current was comparable to that produced by 1-2 open gA channels (ca. 25 pS per channel) for applied potentials between 0-100 mV, which enabled the fast capacitance cancellation to better handle the input and BLM capacitance. Fast capacitance cancellation was therefore employed to suppress large capacitive currents and to some degree the BLM capacitance in subsequent experiments. Second, at a capacitance of ~150 fF, $C_m$ is ca. 10-fold lower than $C_p$. Third, the smaller pipette apertures and reduced $C_m$ resulted in a further decrease in instrument noise. BLMs suspended across 20 µm apertures routinely exhibited 200-250 fA rms noise at 1 kHz when using a 50 GΩ feedback resistor. Comparatively, BLMs suspended across 3 µm aperture pipettes exhibited 90-120 fA rms noise, owing to the reduced capacitance contribution of the BLM to total noise. Due to these advantages, all further studies were performed using pipettes with 3 µm apertures.

Investigation of Voltage Protocols for Rapid Measurement of Membrane Conductance:

An assessment of multistep voltage protocols was performed to examine the influence of the number, magnitude and duration of voltage steps on the measured conductance and the associated total acquisition time. The goal was to identify voltage protocols that reproduced membrane conductance determined using a reference protocol (FIG. 8A), while implementing the fewest potential steps to minimize the acquisition time. FIGS. 8B-8E show four protocols (B-E) that were evaluated, relative to reference protocol A, using DPhPC BLMs on 3 µm aperture pipets. In protocols B-E, the step duration and magnitude were varied from 10-100 ms and 10-100 mV, respectively. Based on the relaxation times, a minimum step length of 10 ms was selected to enable current measurements over several ms.

Membrane conductance values and net conductance acquisition times (defined here as the total time required to acquire a single conductance measurement) measured using protocols A-E are listed in Table 1. The mean conductance values ranged from 3.5-6.9 (×$10^{-3}$) pA/mV and in some cases (e.g., protocols C and E) were statistically distinct from the conductance value obtained using protocol A. This variability is expected, however, because the BLMs exhibited different seal resistances, ranging from 147 GΩ to 284 GΩ. The differences in seal resistance among the pipettes/BLMs used here do not pose an impediment for sensing IC activity because each sensor must be calibrated prior to use for quantitative measurements. Although protocols B-E produced larger relative standard deviations (RSDs) than Protocol A, there was no observed correlation between net conductance acquisition time and RSD (Table 1).

TABLE 1

Comparison of measured conductance of pure DPhPC BLMs on 3 µm pipettes using voltage protocols A-E shown in FIG. 8A-8E.

| Protocol | Conductance [(pA/mV) × $10^{-3}$][a] | Net Conductance Acquisition Time[b] |
|---|---|---|
| A | 4.38 ± 0.12 | 2 s |
| B | 3.54 ± 1.31 | 500 ms |
| C | 5.93 ± 0.78[c] | 60 ms |

TABLE 1-continued

Comparison of measured conductance of pure DPhPC BLMs on 3 μm pipettes using voltage protocols A-E shown in FIG. 8A-8E.

| Protocol | Conductance [(pA/mV) × $10^{-3}$][a] | Net Conductance Acquisition Time[b] |
|---|---|---|
| D | 4.83 ± 1.25 | 60 ms |
| E | 6.78 ± 0.89[c] | 30 ms |

[a]n = 10. Linear correlation coefficients ($r^2$) were 0.97-1.0.
[b]The net conductance acquisition time represents the total time required to obtain a single conductance measurement from an i-V curve.
[c]Statistically significant difference from protocol A (p < 0.05).

Table 1 shows that the BLM conductance can be measured more rapidly, relative to protocol A, using voltage steps of short duration and small magnitude. Comparing protocols B-E, the largest voltage steps (50-100 mV) were used in protocol B and produced the largest steady state currents; however, the capacitive current relaxation time was >10 ms and thus the net conductance acquisition time was the largest. Smaller voltage steps were used in protocols C-E to reduce the net conductance acquisition time. Using three 10 mV voltage steps with a step duration of 10 ms (protocol E) enabled BLM conductance measurements to be made in 30 ms. Thus, further studies were performed with protocol E.

It is important to note that some capacitive charging (<1 pA) is present in the time frame 3-10 ms after application of a 10 mV step. Further reductions in net conductance acquisition time could be achieved by decreasing the magnitude of the voltage step to <10 mV; however, sensor sensitivity also must be considered. The current per IC is the product of the intrinsic IC conductance and the applied potential; thus a lower magnitude will produce an inherently lower S/N ratio. However, this effect could be counterbalanced by increasing the number of ICs in the BLM.

Figure 9A:
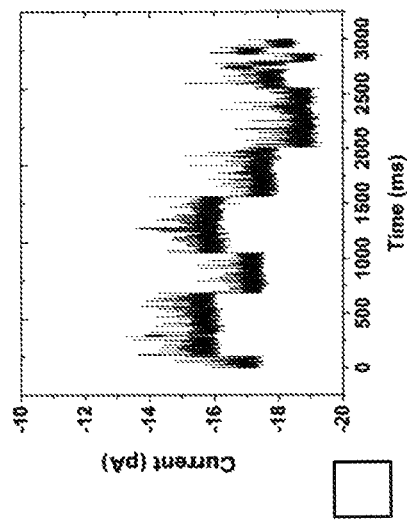
FIG. 9A shows a single channel recording trace for a BLM functionalized with gA at a holding potential of −100 mV.

Conductance Measurements with Gramicidin Functionalized BLMs:

Gramicidin A dimerizes in lipid bilayers to form non-selective, cation-permeable ICs and is widely used as a model IC for illustrating BLM formation. A DPhPC BLM was suspended across a 3 μm pipette aperture and titrated with gA until several channels were continuously active. The conductance of the BLM was measured using protocols A and E with recording buffer on both sides of the membrane. FIG. 9A shows a representative single channel trace at a holding potential of −100 mV where each gA channel contributed ~2 pA of current, and at least eight channels were active. FIG. 9B shows a representative current versus time trace during execution of protocol E. The mean steady state current was calculated during intervals of 3-5 ms and 5-10 ms after the initiation of each voltage step, and the resulting curves are plotted in FIG. 9C along with current measurements obtained using protocol A. Table 2 lists the resulting conductance values, which were statistically equivalent with <5% RSD in all cases.

TABLE 2

Comparison of conductance measured for a gA-functionalized BLM using protocols A and E.

| Protocol | Conductance [pA/mV][a] |
|---|---|
| A | 0.154 ± 0.0018 |
| E[b] | 0.159 ± 0.0062 |
| E[c] | 0.155 ± 0.0045 |

[a]n = 5.
[b]Current was averaged during interval of 3-5 ms after the voltage step was initiated.
[c]Current was averaged during interval of 5-10 ms after the voltage step was initiated.

Overall, these results demonstrate the feasibility of making a statistically valid measurement of the conductance of an IC-functionalized BLM in static solution using a voltage protocol composed of three, smaller amplitude, shorter duration steps in as short as 30 ms. While the primary goal of this work is to develop a method to rapidly measure ligand-induced conductance changes of small conductance, rapid switching channels as sensor transducers, this approach should also be amenable to channels with longer dwell times.

Based on the noise performance of the small aperture geometry BLM/pipette platform (90-120 fA rms noise, 1 kHz) and the intrinsic conductance of a gA channels (21-25 pS), it is estimated that ~2 active channels are required to achieve a S/N≥3 at 10 mV. The BLMs were prepared with >5 gA channels consistently active. Under these conditions, S/N ratios greater than 10 were observed at 10 mV step potentials, the lowest magnitude applied in these conductance protocols.

Figure 9C:
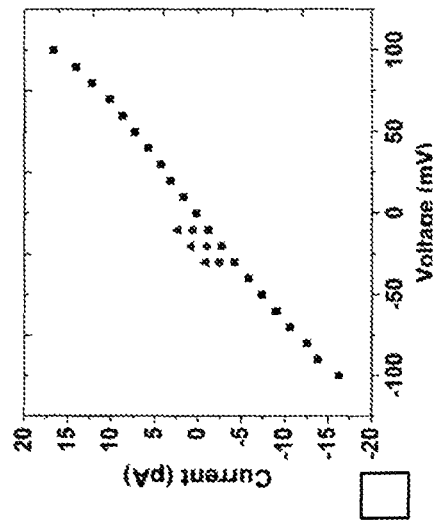
FIG. 9C is a plot of conductance curves obtained using protocols A and E. Mean current was measured during 3-5 ms (blue triangle) and 5-10 ms (red circle) intervals after each voltage step. Curves are offset by 2 pA (red) and 4 pA (blue) for clarity.

Measurement of Fast Solution Exchange with gA-Functionalized BLMs:

To assess the utility of conductance-based measurements for monitoring dynamic changes in IC activity, a rapid solution exchange system was employed to measure the response of a gA-functionalized BLM to $Ca^{2+}$. $Ca^{2+}$ is a potent pore blocker that inhibits gA cation conduction, and was used here as a surrogate for antagonism of a ligand-gated IC. For these experiments, protocol F (FIG. 8F), a continuous acquisition version of protocol E, was used. This protocol was looped 240 times to sample the membrane conductance for 1 min. Voltage steps ranging from −10 to −30 mV were sequentially applied for 10 ms in a recurring, pyramid-like fashion to enable continuous monitoring without resetting the initial voltage to 0 mV and facilitate conductance measurements in both the downward and upward sweeps of the protocol. Eliminating the reset to 0 mV circumvented the large charging incurred when stepping from −30 mV to 0 mV in protocol E (FIG. 8E). Mean current values at each voltage step were obtained by averaging the steady state current between 5-10 ms after the voltage step was initiated. The choice of −10 to −30 mV potential range was arbitrary, as FIG. 9C shows that gA does not exhibit channel rectification between −100 and +100 mV in 1 M KCl buffer.

Figure 11A:
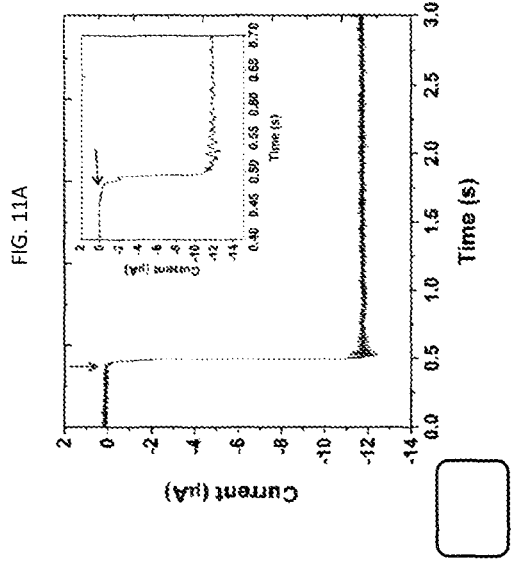
FIG. 11A shows a typical voltage clamp recording for a 3 μm open pipette (no BLM) during rapid solution exchange. The inset shows an expanded view of the switching event (red arrows) when the $Ca^{2+}$ concentration in the perfusion solution was increased from 0 M to 1 M.

Rapid solution exchange between $Ca^{2+}$ and $Ca^{2+}$-free recording buffers was performed using a theta glass capillary with continuous perfusion from two parallel ports (FIG. 1C) directed at the tip of a BLM/pipette. FIG. 11A shows a typical voltage clamp recording using an open pipette (i.e., lacking a BLM) while monitoring current at a holding potential of −20 mV. The outlet of one port of the theta capillary was directed at the open pipette tip, and then the theta capillary tip was mechanically translated to direct the outlet of the other port at the open pipette tip. The 10-90% response time was 12±2 ms (n=7), which reflects the minimum response time that can be measured using this apparatus. Hysteresis observed as ringing in the signal persisted for ca. 100 ms after the solution was exchanged, likely due to the complex fluid flow profile across the BLM/pipette tip.

Figure 10A:
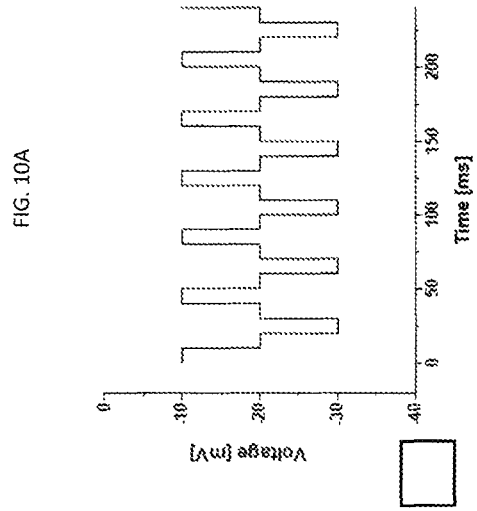
FIG. 10A shows continuous voltage protocol F used to evaluate membrane conductance.
Figure 10B:
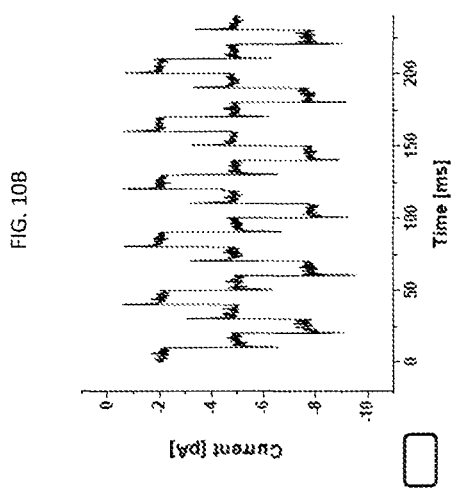
FIG. 10B shows a current trace and FIG. 10C shows a normalized conductance plot resulting from application of protocol F to a gA-functionalized BLM suspended across a 3 μm aperture and perfused with $Ca^{2+}$-free recording buffer.
Figure 10C:
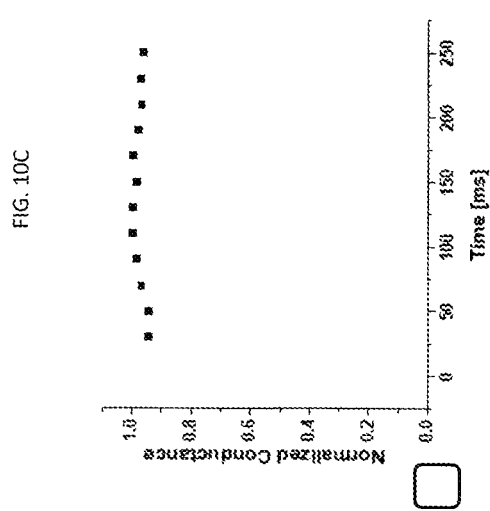

BLMs suspended on 3 μm aperture pipettes were functionalized with gA by adding 1 μL aliquots of 1 pg/mL gA in EtOH to the recording buffer in which the pipette tip was immersed, until 5-20 consistently-active channels were observed. The BLM conductance was measured while the BLM/pipette tip was initially perfused with $Ca^{2+}$-free recording buffer. An example current trace recorded using protocol F and the corresponding conductance vs. time plot are shown in FIGS. 10A-10C. Values of $r^2$ for linear least squares fitting of the individual, three-point conductance curves ranged from 0.98-1.0. The conductance values were statistically equivalent which shows that the direction of the voltage steps (increasing vs. decreasing) had no effect on the measurement.

Figure 11B:
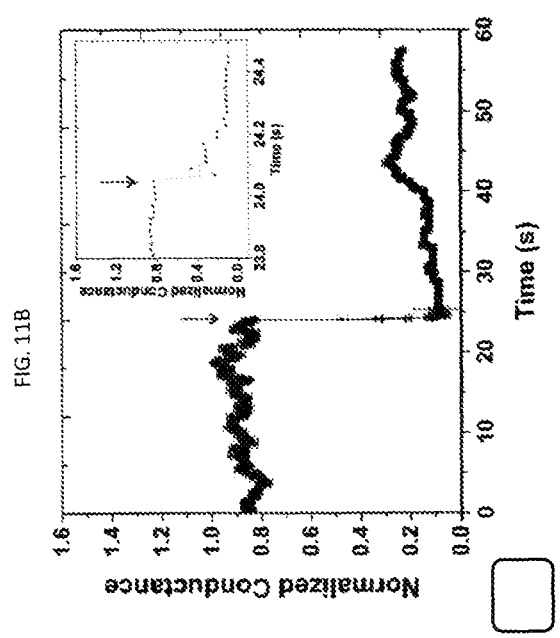
FIG. 11B is a representative conductance vs. time plot for a gA-functionalized BLM/pipette as the $Ca^{2+}$ concentration in the perfusion solution was increased from 0 M to 1 M at ca. 24 seconds. The inset shows an expanded view of the solution switching event (red arrows).

An example conductance vs. time trace showing the effect of mechanically translating the theta capillary tip to direct $Ca^{2+}$-containing buffer to the BLM/pipette tip is plotted in FIG. 11B. A large change in conductance was observed when the $Ca^{2+}$ concentration was increased to 1 M at approximately 24 seconds. To enable comparisons between different trials with differing numbers of ICs, the raw conductance data were normalized to the highest measured conductance within an individual trial. The normalized conductance decreased by greater than 70% within one data point (30 ms) following the step change in $Ca^{2+}$ concentration, although hysteresis in the curve continued out to 150 ms. The hysteresis was similar to that observed in FIG. 11A, suggesting it is related to complex flow patterns in the rapid solution exchange system. Importantly, the immediate decrease in the normalized conductance upon solution exchange was 76.0±7.5% (n=7) and agrees well with the value of 81.9±13.5% obtained using the mean of a 1 s window before and after solution exchange. The fluctuations in conductance prior to $Ca^{2+}$ addition likely result from gA channel formation and dissociation, though these are minor relative to the larger magnitude change associated with $Ca^{2+}$ blockage. For more traditional ligand-gated ICs envisioned for sensor preparation, changes in the number of active channels due to association/dissociation of active monomers would likely be less significant due to the transmembrane nature of these ICs.

Overall, the present invention demonstrates the feasibility of using a conductance-based approach to measure target-induced changes in the activity of an ensemble of ICs with an acquisition time in the ms regime. Rapid measurement of BLM conductance provides a reproducible method for measuring ensemble IC activity at time scales relevant for applications requiring <50 ms temporal resolution. The net conductance acquisition time of this approach is dictated by the duration of each voltage step, the need to measure current at a minimum of three different potentials, and the time course of capacitive charging. The minimum duration of each potential step depends on the decay characteristics of the capacitive charging and the time interval needed to measure the steady state current. For a BLM suspended across ca. 3 μm aperture pipette, the capacitive current relaxes significantly within 1 ms after the voltage step is initiated, and the steady state current can be measured reproducibly in the 5-10 ms interval after the voltage step, or in the 3-5 ms interval if a small decrease in precision is tolerable. Using a three voltage step protocol, a conductance measurement can be made in 30 ms, and further optimization focus on decreasing the input capacitance ($C_p$) could reduce this further. In contrast, a single channel recording may require up to several minutes of data collection to measure IC activity at a given ligand concentration.

Example 2

The following is a non-limiting example of a sub-millisecond conductance protocol for ion channel measurements. Equivalents or substitutes are within the scope of the invention.

Improvements to the glass microaperture platform to realize, low-noise recordings with sub-millisecond response times up to 10 kHz bandwidth are described herein. A modified version of the conductance protocol developed in Example 1 is described which realizes 0.9 ms temporal resolution. Additionally, the capability of the optimized sub-ms conductance protocol to track, with high-fidelity, μs changes in ion concentration is demonstrated. The response time of this ion channel-functionalized biosensor is expected to be suitable for studying single cell exocytosis.

Experimental

The 3 μm glass microapertures were fabricated and the BLMs were formed by the tip dip method as previously described.

Electrophysiology and Noise Measurements:

Electrophysiological data was acquired with a HEKA EPC-10 Single patch clamp amplifier and digitized with Patchmaster software (v. 2.73). Single channel recordings were obtained at a −100 mV holding voltage, digitized at 20 kHz and filtered at 1 kHz, unless otherwise stated. Sub-millisecond conductance measurements were collected at 200 kHz and filtered at 10 kHz. Noise values were obtained from the Noise Panel present in Patchmaster software which measures instrument noise through the amplifier's 4-pole, low-pass Bessel filter.

Noise values for the BLM pipette platform were determined using an established protocol. Sylgard 184, prepared in a 9:1 (w/w) ratio of polymer:curing agent, was added to the bottom of a 35 mm petri dish and allowed to polymerize at 50° C. for 30 min. Several polydimethylsiloxane (PDMS) layers were added until the PDMS approximated a semi-circle. BLM pipettes were backfilled with recording buffer (1 M KCl, 5 mM HEPES, pH ~7.4), mounted onto the headstage, and submerged in the PDMS-containing petri dish also filled with recording buffer. The pipette was slowly brought into contact with PDMS until a change in resistance from kΩ to MΩ was noted, at which point the pipette was lowered in 1 μm steps, until a >50 GΩ seal was formed. Pipettes were generally not depressed >5 μm into the PDMS. Instrument noise was measured over a range of filter frequencies from 100 Hz to 15 kHz. Similar noise measurements were performed on the same pipette after a BLM had been formed. Power spectral density plots were obtained from single channel recording traces at 0 mV holding voltages and converted to frequency space using the Fast Fourier Transform function in Origin Labs software. All measurements were performed at 1 mm immersion depth.

Data Analysis:

Membrane conductance values were evaluated against a 21-point reference protocol that applied a 50 ms voltage pulses ranging from −100 to +100 mV, in 10 mV intervals. Each pulse was preceded by a 10 ms rest at a holding voltage of 0 mV and followed by a 1000 ms rest (0 mV) to ensure the bilayer capacitance was fully discharged before proceeding to the next voltage step. The slope of the i-V curve is the conductance, GBLM (pA/mV); the BLM resistance, RBLM, is (GBLM)-1. For sub-millisecond conductance protocols, protocol E in Example 1 was modified to achieve fast voltage pulses (<1 ms).

Response Time Measurements:

Fast solution switching experiments were performed with a High Speed Solution Exchange-2/3 system (ALA Scientific, New York), A BLM pipette was positioned about 1 mm away and equidistant from the outflow of two tubes approximately perpendicular from one another. Each tube was connected to a solution reservoir containing recording buffer or recording buffer+1 M $Ca^{2+}$. The linear flow rate was ~2 cm/s, as higher flow rates caused BLM delamination. The solution composition perfusing across the BLM pipette was rapidly switched using a solenoid pinch valve and the membrane conductance was measured using the patch clamp amplifier. Membrane conductance was assessed as described above.

Results and Discussion

Figure 12:
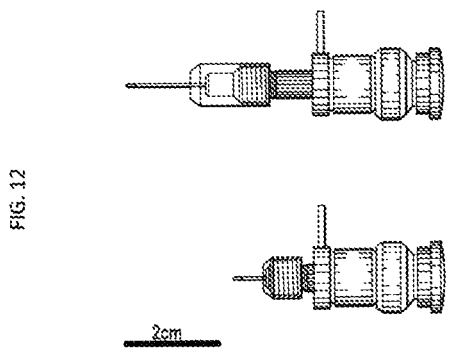
FIG. 12 depicts a non-limiting example of a modified pipette holder which shortens the holder length by ~1.7 cm and the electrode length by ~3 cm.

Fabrication of a Low-Noise BLM Platform:

DPhPC BLMs suspended across 3 μm apertures in PDMS-coated pipettes routinely achieved noise levels of 90-120 fA rms, at a filter setting of 1 kHz. Expansion of the filter bandwidth to 10 kHz to facilitate measurements in the sub-ms regime, a suitable temporal resolution for single-cell exocytosis, introduces additional noise components which affect signal-to-noise ratios. Therefore, the present invention developed an improved architecture for obtaining low-noise recordings up to 10 kHz. As shown in FIG. 12, the improved holder reduces the contribution to ~0.5 pF. The glass pipette contributes ~0.23 pF in air, and ~0.6 pF when the glass pipette is submerged 1 mm in solution. These combined values provide a total input capacitance of 2.2 pF, ~2× smaller than the previous platform. The shortened holder/pipette geometry implemented here provides low-noise recordings up to 10 kHz. Analyses of the total noise contributions indicate that the holder, electrode, and pipette are the major noise contributors. Lower noise recordings may be realized by further reducing the pipette holder and pipette capacitance contributions. Such a strategy will involve additional shortening of the holder and pipette. Furthermore, changing glass type from borosilicate to quartz is expected to further decrease dielectric noise, owing to a dielectric lossiness factor>22 fold lower ($D_{quartz}$~$10^{-5}$-$10^{-4}$) than the Schott 8250 glass (D~$2.2\times10^{-3}$) used in this example. Without wishing to limit the invention to a particular theory or mechanism, the present BLM pipette platform can approach noise levels comparable to quartz patch pipette technologies. However, it is expected that through careful minimization of capacitance contributions, the BLM pipette platforms can reach comparable noise levels to patch clamp experiments.

Figure 13:
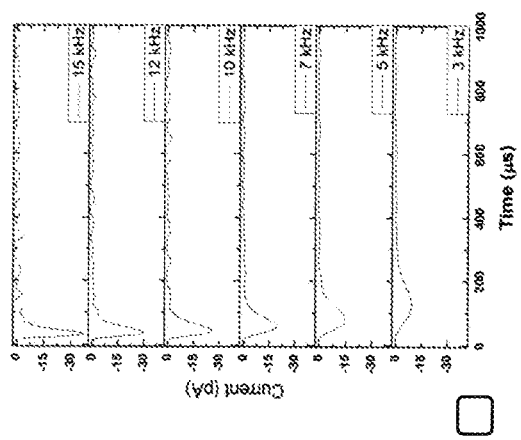
FIG. 13 shows plots of the effects of filtering frequency on BLM platform capacitive charging currents.

Generation of Sub-Ms Conductance Protocols & Evaluation of Gramicidin a Functionalized BLMs:

Sub-millisecond conductance protocols require rapid relaxation (μs) of capacitive charging currents to facilitate fast sampling of steady-state currents resulting from active ion channels. In Example 1, the capacitive charging time course was dominated by the input capacitance at short time regimes, <2 ms with a 1 kHz filter. The 1 kHz filter setting likely aliased faster charging components, thus widening of the filter bandwidth was expected to accelerate apparent capacitive charging time. Protocol E was used as a base voltage program to assess capacitive currents, with slight modification—voltage steps were maintained at 10 mV, but pulse duration was reduced to 1 ms. FIG. 13 illustrates the effects of filter bandwidth on the apparent relaxation time for DPhPC BLMs suspended across the optimized BLM platform. Fast capacitance cancellation was implemented to prevent amplifier saturation; thus, presented current relaxation times do not reflect real charging time constants of the BLM platform. As expected, higher bandwidths correlated with faster charging times: capacitive charging relaxed within ~220 μs at 3 kHz and ~60 μs at 15 kHz. While the fastest charging was observed at 15 kHz, the increased noise levels (>980 fA rms) would detrimentally affect S/N ratios. Therefore, the filter setting was set at 10 kHz, which exhibited a relaxation time of ~100 μs.

The significantly higher noise levels (620-830 fA rms) at 10 kHz compared to 1 kHz bandwidth required reassessment of the number of reconstituted channels needed to produce S/N>3. Gramicidin A was once again used as a model ion channel. An individual gA ion channel increases membrane conductance by ~20 fA/mV in 1 M KCl solutions. Thus, at an applied voltage of 100 mV, a single ion channel has an inherent single channel current of 2 pA (S/N~2.3-3.1), and 0.2 pA (S/N~0.23-0.31) at 10 mV. S/N ratios of ~3, for a 10 mV voltage step, therefore require >10 active channels, based on the platform noise range.

Figure 14A:
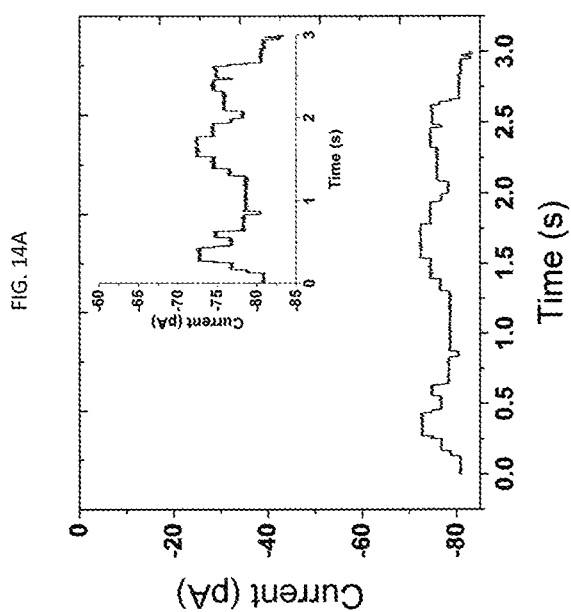
FIGS. 14A-14D shows a representative single channel recordings trace, and voltage step protocol, associated current trace, and steady-state currents.
Figure 14B:
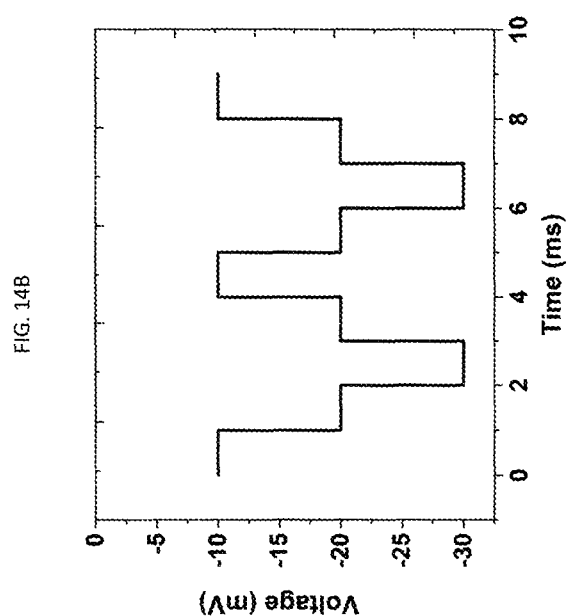
Figure 14C:
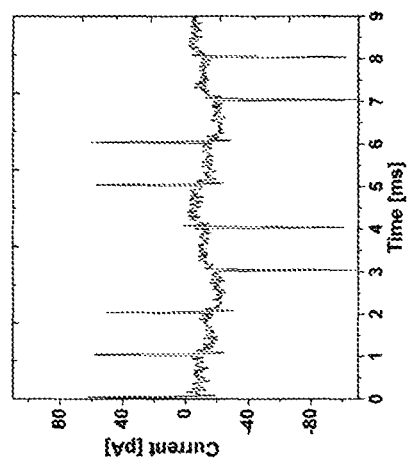
Figure 14D:
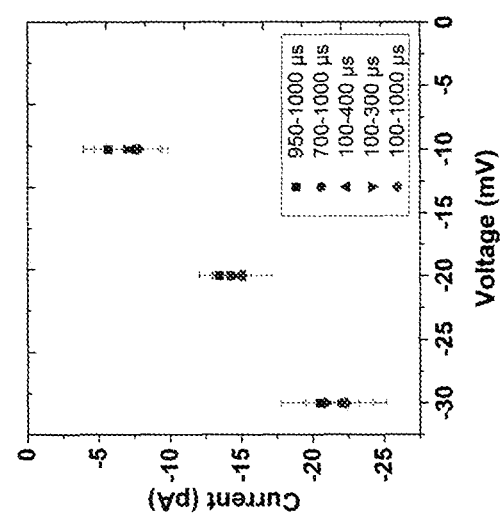

FIG. 14A shows gA activity from a DPhPC bilayer with >30 active channels at a holding potential of −100 mV. Individual opening and closing events were still resolvable despite the large number of reconstituted channels. FIG. 14B shows the voltage protocol applied to the bilayer, employing 10 mV steps at 1 ms duration, to sample membrane currents (FIG. 14C). Membrane currents were averaged at various time points past the charging current and up to 1 ms. FIG. 14D plots the averaged current versus applied potential for several intervals.

The data demonstrated the feasibility of developing fast voltage protocols implementing voltage pulses with short, 300 μs durations. In contrast with Example 1, slower charging currents were not observable at these short time regimes. They are presumably still present; however, they are indistinguishable from the noise at 10 kHz due to their relatively low magnitude. Based on these observations, the voltage protocol in FIG. 14B was optimized to implement 300 μs voltage steps, maintaining 10 mV steps.

Figure 15A:
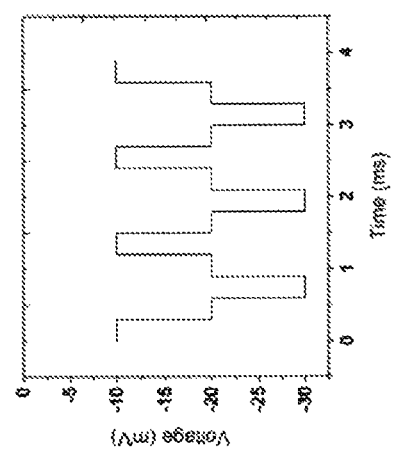
FIG. 15A-15B shows voltage protocols used to evaluate membrane conductance in Table 3.
Figure 15B:
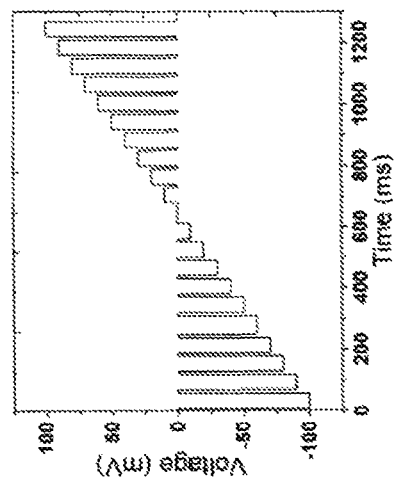

FIG. 15A shows the optimized sub-ms voltage protocol versus time, which now has a response time of 0.9 ms. For reference, FIG. 15B shows a typical reference voltage protocol. Membrane conductance for gA-functionalized DPhPC BLMs was measured using the optimized, sub-millisecond voltage protocol and compared against a 21-point reference protocol in static solution. TABLE 3 shows that both protocols report statistically equivalent membrane conductances for n=5 consecutive measurements. This result illustrates the ability of the optimized sub-ms conductance protocol to recapitulate, with high fidelity and significantly better temporal resolution, membrane conductance measurements obtained from slower protocols. Compared to the BLM platform and voltage protocol described in Example 1, the platform and protocol described here achieves 33× increase in temporal resolution with ~6× increase in total noise, for 10× increase in instrument bandwidth. The 0.9 ms response time of this IC-sensor platform is expected to provide sufficient resolution to facilitate study of single cell exocytosis.

TABLE 3

Comparison of membrane conductance values calculated from different voltage protocols.

| | Traditional Voltage Protocol | Sub-ms Voltage Protocol |
|---|---|---|
| Average Conductance [pA/mV] | 0.65 + 0.07 (n = 5) | 0.68 + 0.04 (n = 5) |
| Response Time | >1 s | 0.9 ms |

High Speed Solution Exchange Demonstrates Fast Ion Channel Conductance Measurements:

To demonstrate the feasibility of monitoring abrupt changes in ligand concentration in the sub-ms to ms time regime, a commercially available fast solution exchange system was used to rapidly apply a $Ca^{2+}$ solution ($t_{20-80\%}$<1 ms) across a gA-functionalized BLM. In contrast to the dual perfusion tip employed in Example 1, this system uses a fast switching solenoid valve to control flow through two applicator tubes. The low dead volume of the tubing, coupled with the relatively fast linear flow rate of solution (~2 cm/s) enable fast solution exchange across the BLM pipette positioned at the crosshairs of the outlets. The 10-90% response time was 700 µs-1 ms (n=7), depending on the position of the pipette and solution height.

Figure 16:
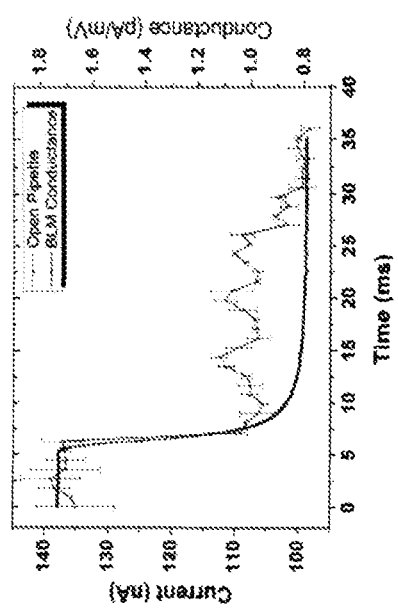
FIG. 16 is a measurement of fast solution exchange with gA-functionalized BLMs. The open pipette (black squares) shows the solution switching time has $t_{20-80\%}$~700 μs. BLM conductance measurements were roughly aligned and superimposed on open pipette currents. The red arrow indicates the point of solution switching from recording buffer to 1 M $Ca^{2+}$.

After establishing the optimal solution switching position, a DPhPC BLM was formed across the aperture, and then functionalized with gA channels. The pipette was repositioned at the optimal switching position, with recording buffer flowing across the pipette tip. After ~20 s of data collection, the solution was switched to recording buffer supplemented with 1 M $Ca^{2+}$. FIG. 16 shows overlapped traces for the open pipette tip response and the membrane conductance for gA-functionalized BLMs upon switching solution compositions. Membrane conductance decreased ~60% upon application of 1 M $Ca^{2+}$. Largely, the membrane conductance response follows the open pipette tip response, except for a lag lasting ~25 ms upon solution switching. It is suspected that the non-perpendicular positioning of pipette relative to the solution outlets, along with the relatively high flow velocities, causes BLM curvature. This phenomenon generates a low volume reservoir which does not efficiently exchange solution with flow streams. This problem may be fixed by applying a counter pressure in the pipette interior to reverse membrane curvature. However, in single cell exocytosis studies, the relatively low solution flow rates are not expected to induce membrane curvature.

Overall, lowering the overall capacitance of the BLM platform enabled an increase in instrument bandwidth from 1 kHz to 10 kHz, with ~6-8× increase in total noise (620-830 fA rms). This noise range is only 2.2-3.1× the noise of a shielded headstage, and may represent one of the lowest reported noise values for a BLM system to date at 10 kHz. Additional reductions in noise may be aided by further lowering capacitance contributions from the holder and pipette and the use of low dielectric lossiness material, e.g. quartz pipettes. The extended bandwidth and fast capacitance cancellation facilitated rapid relaxation of capacitive charging currents to <100 µs. Based on these results, an optimized voltage protocol was developed, employing 3 voltage steps at 300 µs duration at each step, and enabling membrane conductance measurements every 0.9 ms. The 0.9 ms response time of this low-noise, IC-sensor platform is expected to provide sufficient resolution to facilitate study of single cell exocytosis.

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are represen-tative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

What is claimed is:

1. A method of obtaining ion channel measurements from an ion channel (IC) functionalized sensor platform, said method comprising:
    a. providing the IC-functionalized sensor platform comprising a pipette and a lipid membrane suspended on a pipette aperture of the pipette, wherein a plurality of ion channels is embedded in the lipid membrane, wherein the IC-functionalized sensor platform is operatively connected to an amplifier;
    b. placing the IC-functionalized sensor platform in a solution such that the lipid membrane is disposed in the solution;
    c. continuously applying a voltage set to the IC-functionalized sensor platform via the amplifier, wherein the voltage set comprises a plurality of consecutive voltages that are applied in a step-wise pattern so as to alternate between decreasing and increasing voltages, wherein each voltage is rapidly applied for a short duration pulse; and
    d. measuring a conductance of the lipid membrane; wherein a net time required for measuring the conductance is about 0.5 msec to about 50 msec.

2. The method of claim 1, wherein a diameter of the pipette aperture is about 1-5 µm.

3. The method of claim 1, wherein the voltage set comprises about 2-5 increasing voltage steps and about 2-5 decreasing voltage steps.

4. The method of claim 3, wherein each voltage step ranges from about 5-15 mV.

5. The method of claim 1, wherein the short duration pulse ranges from about 5-15 ms.

6. The method of claim 1, wherein the lipid membrane comprises at least about 5 consistently active ion channels.

7. The method of claim 1, wherein the pipette aperture is silanized.

8. The method of claim 1, wherein the pipette aperture is coated with a siloxane compound.

9. The method of claim 1, further comprising a step of adding an analyte to the solution, wherein measuring the conductance comprises measuring a first conductance after the analyte is added to the solution.

10. The method of claim 9, wherein measuring the conductance further comprises measuring a second conductance before the analyte is added to the solution.

11. A method of obtaining ion channel measurements from an ion channel (IC) functionalized sensor platform, said method comprising:
    a. providing the IC-functionalized sensor platform comprising an apparatus with an aperture and a lipid membrane suspended on the aperture, wherein a plurality of ion channels is embedded in the lipid membrane, wherein the IC-functionalized sensor platform is operatively connected to an amplifier;
    b. placing the IC-functionalized sensor platform in a solution such that the lipid membrane is disposed in the solution;
    c. continuously applying a voltage set to the IC-functionalized sensor platform via the amplifier, wherein the voltage set comprises a plurality of consecutive voltages that are applied in a step-wise pattern so as to alternate between decreasing and increasing voltages, wherein each voltage is rapidly applied for a short duration pulse; and d. measuring a conductance of the lipid membrane; wherein a net time required for measuring the conductance is about 0.5 msec to about 50 msec.

12. The method of claim 11, wherein a diameter of the aperture is about 1-5 μm.

13. The method of claim 11, wherein the voltage set comprises about 2-5 increasing voltage steps and about 2-5 decreasing voltage steps.

14. The method of claim 13, wherein each voltage step ranges from about 5-15 mV.

15. The method of claim 11, wherein the short duration pulse ranges from about 5-15 ms.

16. The method of claim 11, wherein the lipid membrane comprises at least about 5 consistently active ion channels.

17. The method of claim 11, wherein the aperture is silanized.

18. The method of claim 11, wherein the aperture is coated with a siloxane compound.

19. The method of claim 11, further comprising a step of adding an analyte to the solution, wherein the measuring the conductance comprises measuring a first conductance after the analyte is added to the solution.

20. The method of claim 19, wherein the measuring the conductance further comprises measuring a second conductance before the analyte is added to the solution.

* * * * *